(12) United States Patent
Dininno et al.

(10) Patent No.: US 6,255,300 B1
(45) Date of Patent: *Jul. 3, 2001

(54) CARBAPENEM ANTIBACTERIAL COMPOUNDS, COMPOSITIONS CONTAINING SUCH COMPOUNDS AND METHODS OF TREATMENT

(75) Inventors: Frank P. Dininno, Old Bridge; Kevin D. Dykstra, West Milford, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,629

(22) Filed: Dec. 7, 1999

Related U.S. Application Data

(63) Continuation of application No. 09/133,123, filed on Aug. 12, 1998, now abandoned.
(60) Provisional application No. 60/058,223, filed on Sep. 9, 1997.

(51) Int. Cl.$^7$ .................. C07D 477/14; A61K 31/4195; A61K 31/4178; A61K 31/407; A61P 31/04
(52) U.S. Cl. ...................... 514/210.09; 540/302
(58) Field of Search ................ 540/302; 514/210.09

(56) References Cited

U.S. PATENT DOCUMENTS

| | | | |
|---|---|---|---|
| 4,309,438 | 1/1982 | Christensen et al. | 514/210 |
| 4,479,947 | 10/1984 | Christensen | 514/210 |
| 5,607,928 | 3/1997 | Arnould | 514/210 |

FOREIGN PATENT DOCUMENTS

| | | |
|---|---|---|
| 0 007 614 | 2/1980 | (EP) . |
| 0 072 014 | 2/1983 | (EP) . |

OTHER PUBLICATIONS

S. M. Schmitt et al., *J. Antibiotics*, 41(6), pp 780–787 (1988).
W. M. Stanley et al., *JACS*, 55, p 706 (1933).
D. L. Hughes, *Organic Reactions*, John Wiley & Sons, USA., 42 p 335–692, (1992).
H. Finch et al., *Tet Ltrs.*, 34(51), p 8352–8356 (1993).
Arnould et al., *Bioorganic & Medicinal Chemistry Ltrs.*, 6(20), p 2449–2454 (1966).

*Primary Examiner*—Mark L Berch
(74) *Attorney, Agent, or Firm*—Sylvia A. Ayler; Mark R. Daniel

(57) ABSTRACT

The present invention relates to carbapenem antibacterial agents in which the carbapenem nucleus is substituted at the 2-position with an iodo-substituted phenyl linked through a $CH_2$—O— group. The compounds of the invention are represented by formula I:

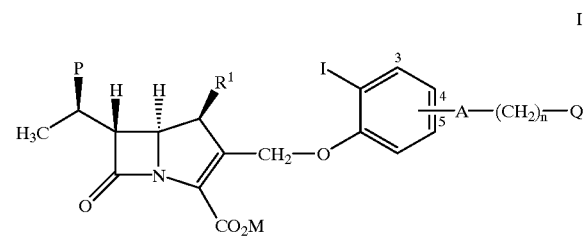

wherein A represent O, S or —$CH_2$— attached at position 3, 4 or 6; Q is selected from the group consisting of:

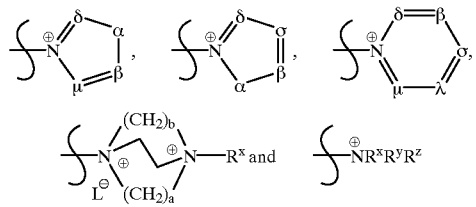

$\alpha$ represents O, S or $NR^s$; $\beta$, $\delta$, $\gamma$, $\mu$ and $\sigma$ represent $CR^r$, N or $N+R^s$, provided that no more than one of $\beta$, $\delta$, $\gamma$, $\mu$ and $\sigma$ is $N+R^s$, balanced by $L^-$ or a carboxylate anion. Salts and hydrates thereof are included. The iodo-substituted phenyl ring is further substituted with various substituent groups including at least one cationic group. Pharmaceutical compositions and methods of treatment are also included.

15 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional application Ser. No. 60/058,223, filed Sep. 9, 1997. This application is also a continuation of Ser. No. 09/133,123 filed Aug. 12, 1998, abandoned.

BACKGROUND OF THE INVENTION

The present invention relates to carbapenem antibacterial agents in which the carbapenem nucleus is substituted at the 2-position with an iodo-substituted phenyl linked through a $CH_2$—O— group. The iodo-substituted phenyl ring is further substituted with various substituent groups including at least one cationic group.

The carbapenems of the present invention are useful against gram positive microorganisms, especially methicillin resistant Staphylococcus aureus (MRSA), methicillin resistant Staphylococcus epidermidis (MRSE), and methicillin resistant coagulase negative Staphylococci (MRCNS). The antibacterial compounds of the present invention thus comprise an important contribution to therapy for treating infections caused by these difficult to control pathogens.

There is an increasing need for agents effective against such pathogens (MRSA/MRCNS) which are at the same time relatively free from undesirable side effects.

SUMMARY OF THE INVENTION

The compounds of the invention are represented by formula I:

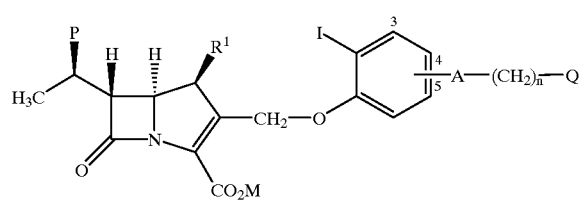

I as well as salts and hydrates thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by hydroxyl-protecting group;

A represents O, S or —$CH_2$— attached at position 3, 4 or 5;

n represents an integer 0–3;

Q is selected from the group consisting of:

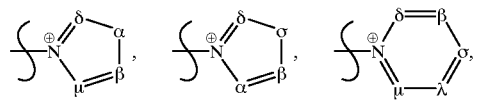

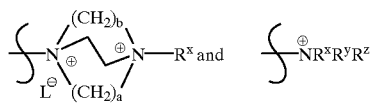

wherein:

a and b are 1, 2 or 3;

L— is a pharmaceutically acceptable counterion;

α represents O, S or NRS;

β, δ, ↓, μ and σ represent $CR^t$, N or $N+R^s$, provided that no more than one of β, δ, ↓, μ and σ is $N+R^s$ balanced by L;, as defined above;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

each $R^i$ independently represents halo; —CN; —$NO^2$; phenyl; —$NHSO_2R^h$; —$OR^h$, —$SR^h$; —$N(R^h)_2$; —$N+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_5$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, NRW or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-5}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N+R^hR^w$ or —C(O)—;

or $R^x$ and $R^y$ together with any intervening atoms represent a 4–6 membered saturated ring optionally interrupted by O, S, $SO_2$, $NR^w$, $N+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O S, $NR^w$ or —C(O)—, said rings being unsubstituted or substituted with one to four $R^i$ groups.

Pharmaceutical compositions and methods of treatment are also included.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and napbthyl.

The term "heteroaryl" refers to a monocyclic aromatic group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

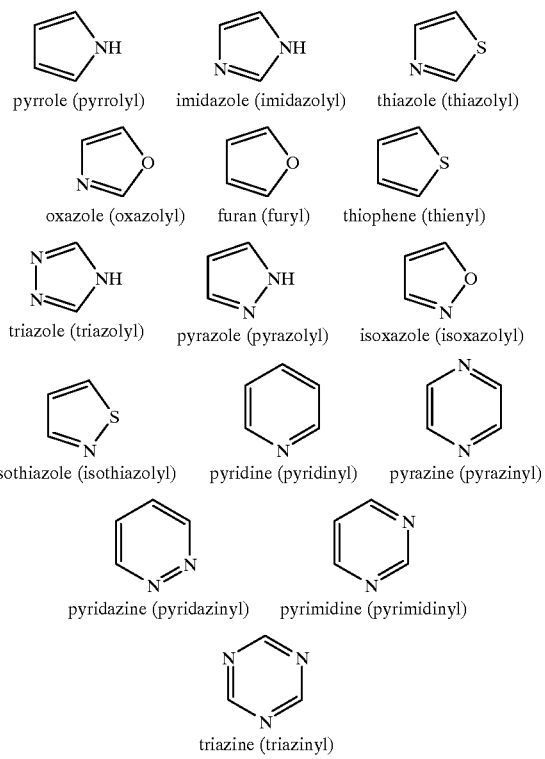

Heteroarylium refers to heteroaryl groups bearing a quaternary nitrogen atom and thus a positive charge. Examples include the following:

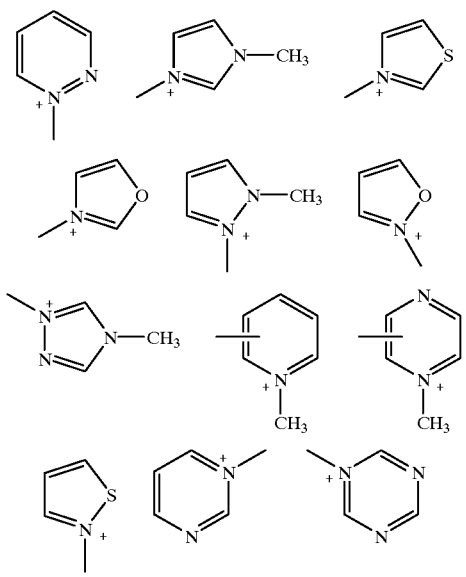

-continued

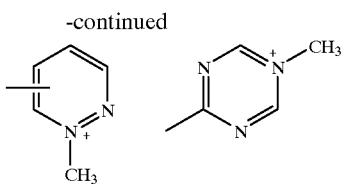

When a charge is shown on a particular nitrogen atom in a ring which contains one or more additional nitrogen atoms, it is understood that the charge may reside on a different nitrogen atom in the ring by virtue of charge resonance that occurs.

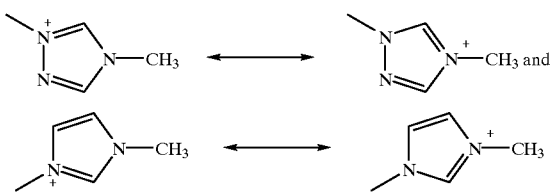

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O-, with the alkyl group optionally substituted as described herein.

Guanidinyl refers to the group: $H_2NC(NH)NH-$.

Carbamimidoyl refers to the group: $H_2NC(NH)-$.

Ureido refers to the group: $H_2NC(O)NH-$.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxy-carbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the phannacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group).

The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

L- can be present or absent as necessary to maintain the appropriate charge balance. When present, L- represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L- represents a specie with more than one negative charge, such as malonate, tartrate or ethylenediamine-tetraacetate (EDTA), an appropriate number of carbapenem molecules can be found in association therewith to maintain the overall charge balance and neutrality.

At least one of the R groups attached to the phenyl ring contains a positively charged moiety.

A subset of compounds of the invention which is of particular interest is described with reference to formula I wherein $R^1$ represents methyl. Within this subset, all other variables are as originally defined.

Another subset of compounds of the invention which is of particular interest is described with reference to formula I wherein $CO_2M$ represents a carboxylic acid or a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of the invention which is of particular interest is described with reference to formula I wherein P represents hydroxyl or hydroxyl protected by hydroxyl-protecting group. Within this subset, all other variables are as originally defined.

Another subset of compounds of the invention which is of particular interest is described with reference to formula I wherein A represents —$CH_2$—. Within this subset, all other variables are as originally defined.

Another subset of compounds of the invention which is of particular interest is described with reference to formula I wherein n represents 0 or 1. Within this subset, all other variables are as originally defined.

Another subset of compounds of the invention which is of particular interest is described with reference to formula I wherein Q represents

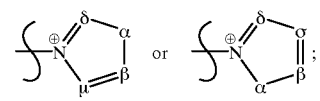

$\alpha$ represents O, S or $NR^s$; and $\beta$, $\delta$, $\gamma$, $\mu$ and $\sigma$ represent $CR^t$, N or $N+R^s$, provided that no more than one of $\beta$, $\delta$, $\gamma$, $\mu$ and $\sigma$ is $N+R^s$, balanced by $L^-$ which is a pharmaceutically acceptable counterion, and $R^s$ is as originally defined. Within this subset, all other variables are as originally defined.

Another subset of compounds of the invention which is of particular interest is described with reference to formula I wherein Q is selected from the group consisting of:

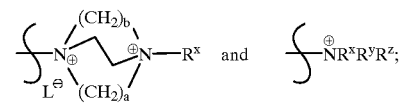

a and b are 2;
$L^-$ is a pharmaceutically acceptable counterion;
and $R^x$, $R^y$ and $R^z$ are as originally defmed.
Within this subset, all other variables are as originally defined.

A more preferred subset of compounds of the invention which is of interest is described with reference to formula I wherein Q is

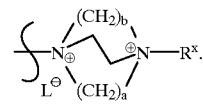

Within this subset, all other variables are as originally defined.

Another subset of compounds of the invention which is of particular interest is described with reference to formula I wherein Q is

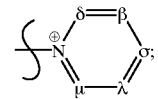

wherein:

α represents O, S or NR$^s$;

β, δ, γ, μ and σ represent CR$^t$, N or N+R$^s$, provided that no more than one of β, δ, γ and σ is N+R$^s$, balanced by L$^-$, which is a pharmaceutically acceptable counterion, and all other variables are as originally defined.

Representative examples of compounds of the invention are as follows:

TABLE 1

| Cpd No. | A-(CH$_2$)$_n$-Q |
|---|---|
| 1 | 4- (1-methylimidazolium-3-ylmethyl) |
| 2 | 5- (1-methylimidazolium-3-ylmethyl) |
| 3 | 3- (1-methylimidazolium-3-ylmethyl) |
| 4 | 5- (1-methylimidazolium-3-ylmethyl) |
| 5 | 4- (1-methylimidazolium-3-ylbutyl) |
| 6 | 4- (1-(2-cyanoethyl)imidazolium-3-ylethyl) |
| 7 | 4- (2-amino-1-ethylpyridinium) |

TABLE 1-continued

| Cpd No. | A-(CH$_2$)$_n$-Q |
|---|---|
| 8 | 4- (DABCO-CH$_2$C(O)NH$_2$, ethyl, OTf$^-$) |
| 9 | 5- (DABCO-CH$_2$C(O)NH$_2$, ethyl, Cl$^-$) |
| 10 | 3- (DABCO-CH$_2$C(O)NH$_2$, ethyl, Cl$^-$) |
| 11 | 4- (DABCO-CH$_2$C(O)NH$_2$, propyl, Cl$^-$) |
| 12 | 4- (DABCO-CH$_2$C(O)NH$_2$, butyl, Cl$^-$) |

TABLE 1-continued

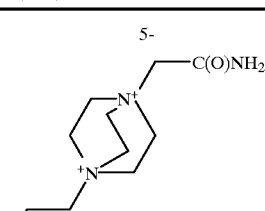

| Cpd No. | A-(CH₂)ₙ-Q |
|---|---|
| 13 | 5- 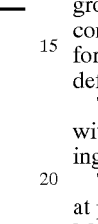 |

The compounds of the present invention are prepared by reacting a suitably protected, activated 2-hydroxymethyl-carbapen-2-em-3-carboxylate with an appropriately substituted phenyl ring, and then removing any protecting groups which are present to afford the desired final product. The process is illustrated by the following generic scheme:

FLOW SHEET A

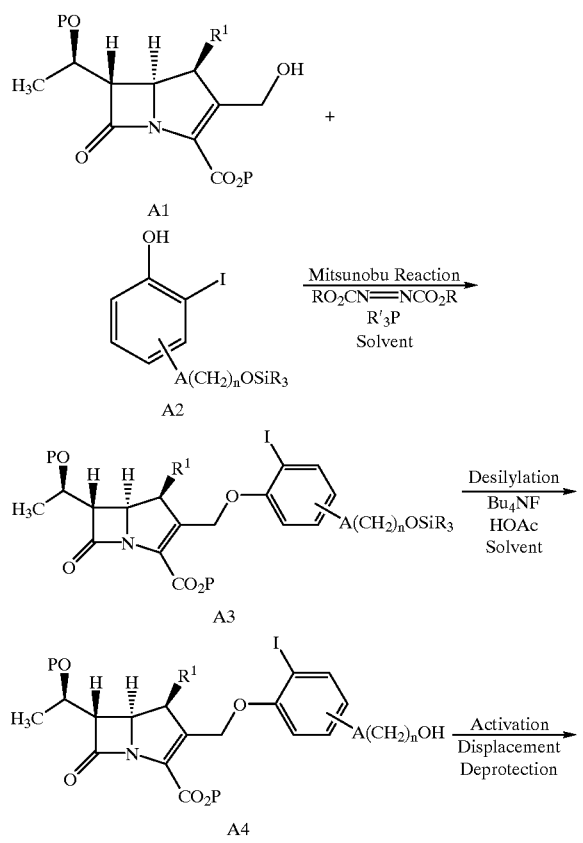

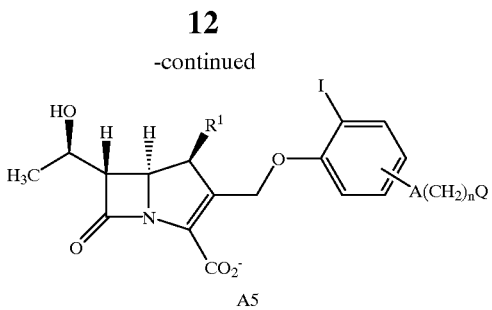

With reference to Flow Sheet A above, P is a protecting group; $R_3$ represents three alkyl or aryl groups which in combination with the silyl group to which they are attached, form a hydroxyl protecting group. $R^1$, A, Q and n are as defined with respect to the compounds of formula I.

The substituted phenyl side chain A2 is initially reacted with a suitably protected carbapen-2-em-3-carboxylate having an activated hydroxymethyl group at the 2-position.

The carbapenem nucleus having a —CH₂OH substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as pnitrobenzyl (PNB), allyl, p-methoxybenzyl, trichloroethyl, 2-trimethylsilylethyl and the like. Furthermore, the hydroxyl group of the 6-(hydroxyethyl) side-chain is protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxycarbonyl, 2-trichloroethoxycarbonyl and the like.

The addition of the quaternary side chain group to the carbapenem is accomplished by treating a solution of the hydroxymethyl-carbapenem A1 and the side chain A2 in a suitable solvent such as tetrahydrofuran (THF), ether, acetonitrile, dimethylformamide (DMF), benzene, dimethylsulfoxide (DMSO), and the like with a (premixed) suitable activating reagent such as diethylazodicarboxylate (DEAD)/ triphenylphosphine, diisopropyl azodicarboxylate (DIAD)/ tributylphosphine, and the like, at a temperature between about −20° C. and 35° C. for about 5 to 90 minutes.

Alternatively, the side chain and carbapenem nucleus can be mixed together with either the azodicarboxylate or the phosphine reagent in a suitable solvent and the other component of the activating reagent (the pbosphine or the azodicarboxylate, respectively) can be added to that mixture. Once the side chain, carbapenem and activating reagent(s) have been mixed, the reaction is allowed to proceed at a temperature between about −20° C. and 35° C. for about 5 to 90 minutes.

The resulting mixture is then subjected to a standard work-up procedure to afford a crude methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

Modification of the side chain, which is generally necessary to introduce the charged substituent, is best accomplished before removal of the protecting groups on the hydroxyethyl side chain or 3-carbapenem carboxylate. For compounds which contain a hydroxyl group in the side chain, a positively charged substituent may be introduced into the side chain by first activating the hydroxyl group. This entails converting it to a suitable leaving group such as a triflate, mesylate, tosylate, iodide, chloride, bromide, and the like, and then displacing the resulting leaving group with a compound, such as N-methyl-imidazole, N-(2-hydroxyethyl)-imidazole, N-methyl-diazabicyclooctane, 1-(carbamoylmethyl)4-aza- 1-azoniabicyclo[2.2.2]octane, 1-(3-hydroxyprop-1-yl)4-aza-1-azoniabicyclo[2.2.2]octane, pyridine, morpholine and the like which contains a nitrogen atom that can act as a nucleophile.

Alternatively, in some cases, the charged substituent may be incorporated in the side chain before addition of the side chain to the carbapenem, or may be introduced after deprotection. However, introduction of the charged before deprotection is greatly preferred.

In some cases, activation of the hydroxyl group and displacement by Q to produce A5 may be accomplished in a single step by taking advantage of the basic character of compound Q and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, 2,6-lutidine, diisopropylethylamine and the like at a temperature between about −100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO and the like as described in the preceding paragraphs. The resulting activated intermediate is treated with 1–3 molar equivalents of compound Q at a temperature between about −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q⁺. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains that contain a nitrogen atom which may be quaternized by reaction with a suitable alkylating reagent, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

The synthesis of the target compound is completed by removing any protecting groups which are present in the penultimate intermediate using standard techniques. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampoules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DCP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

EXAMPLE 1

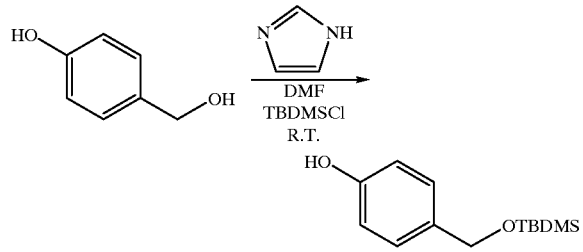

500 mg (4.03 mmoles) of commercially available 4-hydroxybenzyl alcohol was dissolved in 5.0 ml of anhydrous DMF, placed in an $N_2$ atmosphere and chilled to 0° C. To the stirred DMF solution, 301 mg (4.33 mmoles) of imidazole was added followed by 604 mg (4.03 mmoles) of t-butyldimethylsilyl-chloride. The reaction was warmed to ambient temperature and stirred for 18 hrs.

The reaction mixture was extracted with ethyl acetate and partitioned with $H_2O$-dilute aq. sodium bicarbonate and sat. brine. The ethyl acetate extract was dried with anhydrous sodium sulfate and concentrated in vacuo to provide a viscous oil.

The crude product was purified via flash chrom. (230–400 mesh silica gel) and was eluted with a 4:1 mixture of hexanes: ethyl acetate to afford 908 mg of the silyl ether.

$^1$H NMR (CDCl$_3$) δ: 0.10 (s, 6H), 0.94 (s, 9H), 4.66 (s, 2H), 6.08 (s, 1H), 6.72 (d, J=7.5 Hz, 2H), 7.14 (d, J=8.7 Hz, 2H).

EXAMPLE 2

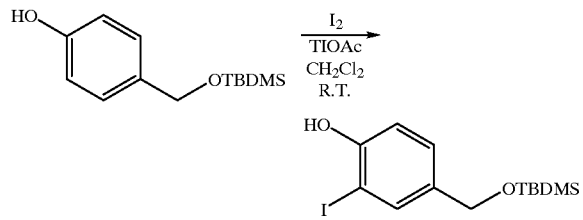

100 mg (0.418 mmoles) of the 4-hydroxy-silyl-ether was dissolved in 2.0 ml of sieve dried dichloromethane and placed in an $N_2$ atmosphere. To the stirred dichloromethane solution, 109 mg (0.418 mmoles) of thallium acetate was added and the tan suspension was stirred for 5 min. at ambient temperature. 109 mg (0.813 mmoles) of iodine was then added. The purple suspension was stirred for 2hrs. and was filtered through a celite plug and was rinsed with 20 ml of ethyl acetate.

The ethyl acetate extract was partitioned with $H_2O$-ice and 5% aq. sodium thiosulfate and sat. brine. The extract was dried with andydrous sodium sulfate and concentrated in vacuo to provide 108 mg of a tan solid.

The crude product was purified using plate layer chromatography with a 4:1 hexanes: ethyl acetate eluent to provide 145 mg of the iodophenol.

¹H NMR (CDCl3) δ: 0.07. (s, 6H), 0.90 (s, 9H), 4.60 (s, 2H), 5.18 (s, 1H), 6.91 (d, J=8.3 Hz, 1H), 7.15 (dd, J=1.9 Hz, 6.3 Hz, 1H), 7.58 (d, J=3.0 Hz, 1H).

EXAMPLE 3

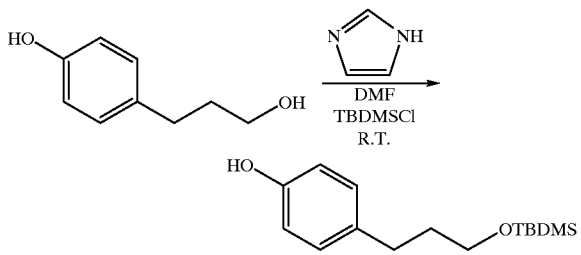

Using the analogous procedure of example 1, the the carbinol was converted to the silyl ether.

EXAMPLE 4

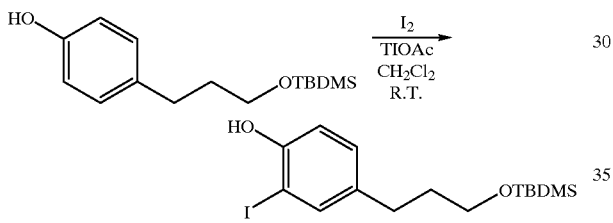

Using the analogous procedure of example 2, the phenol was converted to the iodophenol.

¹H NMR (CDCl₃) δ: 0.06 (s, 6H), 0.91 (s, 9H), 1.68 (m, 2H), 2.55 (t, J=6.7 Hz, 2H), 3.58 (t, J=6.3 Hz, 2H), 5.22 (s, 1H), 6.88 (d, J=8.2 Hz, 1H), 7.05 (dd, J=2.0 Hz, 6.3 Hz, 1H), 7.48 (d, J=2.0 Hz, 1H).

EXAMPLE 5

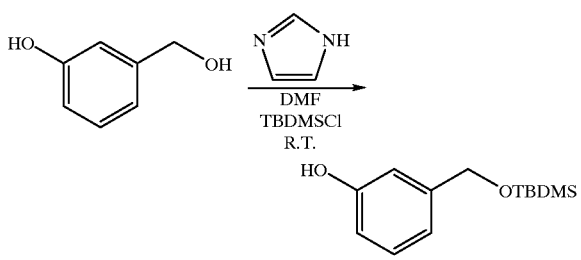

Using the analogous procedure of example 1, the carbinol was converted to the silyl ether.

¹H NMR (CDCl₃) δ: 0.12 (s, 6H), 0.96 (s, 9H), 5.72 (s, 2H), 6.70 (dd, J=1.9 Hz, 4.7 Hz, 1H), 6.83–6.88 (m, 2H), 7.16 (t, J=7.7 Hz, 1H).

EXAMPLE 6

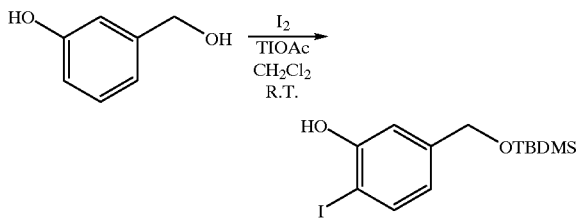

Using the analogous procedure of example 2, the phenol was converted to the iodophenol.

¹H NMR (CDCl₃) δ: 0.10 (s, 6H), 0.94 (s, 9H), 4.66 (s, 2H), 5.29 (s, 1H), 6.66 (dd, J=1.9 Hz, 4.7 Hz, 1H), 6.97 (d, J=2.0 Hz, 1H), 7.56 (d, J=7.3 Hz, 1H).

EXAMPLE 7

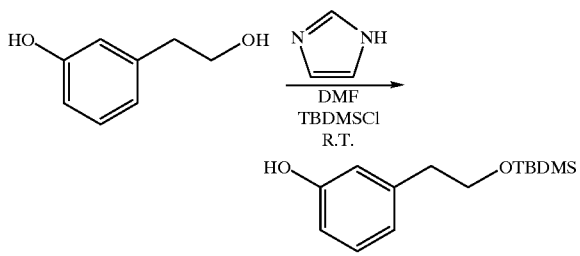

Using the analogous procedure of example 1, the carbinol was converted to the silyl ether.

¹H NMR (CDCl₃) δ: 0.08 (s, 6H), 0.88 (s, 9H), 2.76 (t, J=7.2 Hz, 2H), 3.78 (t, J=7.2 Hz, 2H), 6.65–6.69 (m, 2H), 6.76 (d, J=7.4 Hz, 1H), 7.12 (t, J=6.5 Hz, 1H).

EXAMPLE 8

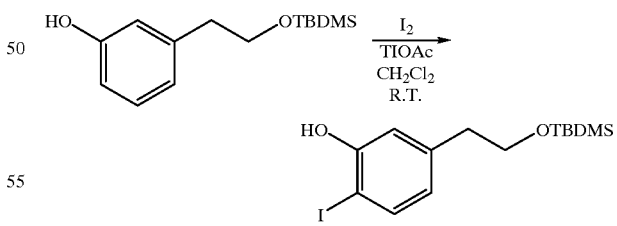

Using the analogous procedure of example 2, the phenol was converted to the iodophenol.

¹H NMR (CDCl₃) δ: 0.10 (s, 6H), 0.88 (s, 9H), 2.72 (t, J=7.0 Hz 2H), 3.77 (t, J=6.9 Hz, 2H), 5.49 (s, 1H), 6.53 (dd, J=2.0 Hz, 6.1Hz, 1H), 6.89 (d, J=2.0 Hz, 1H), 7.52 (d, J=8.0 Hz, 1H).

EXAMPLE 9

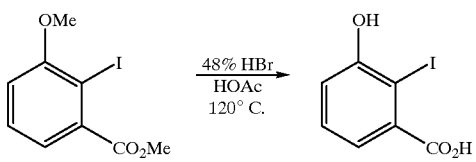

500 mg (1.712 inmoles) of the methyl ester (Stanley, W., M.; McMahan, E.; Adams, R. *JACS*, 1933, 55, 706) was dissolved in 2.9 ml of 48% HBr and 1.49 ml of acetic acid and was placed in an $N_2$ atmosphere. The reaction was stirred for 4 hrs. at 120° C. The cooled reaction mixture was basified to pH 10.0 with 2 ml of 5N aq. sodium hydroxide and partitioned with ethyl acetate-$H_2O$ and ice. The aq. layer was saved and acidified to pH 2.5 with 2.0 N aq. hydrochloric acid, forming a white solid that precipitated from solution. The solid was collected in a sintered glass funnel, washed with 10 ml of deionized $H_2O$ and dried in vacuo to provide 286 mg of benzoic acid.

$^1$H NMR ($d_6$-$Me_2CO$) δ: 7.06 (m, 1H), 7.29 (t, J=8.0 Hz, 1H), 7.51 (dd, J=1.5 Hz, 5.9 Hz, 1H).

EXAMPLE 10

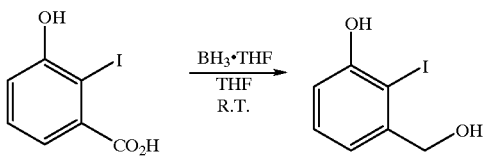

286 mg (1.08 mmoles) of benzoic acid was dissolved in 5.0 ml of anhydrous THF and was placed in an $N_2$ atmosphere. To the stirred THF solution, 2.16 ml of borane-THF complex was added dropwise over 20 min. and the reaction was stirred for 2 hrs. at ambient temperature. 10 ml of methanol was then added to the THF solution slowly over 1 hr.

The reaction was extracted with ethyl acetate and partitioned with $H_2O$-ice and sat. brine. The ethyl acetate extract was dried with anhydrous sodium sulfate and concentrated in vacuo to dryness.

The crude product was purified using silica gel plate layer chromatography eluted with a 7:3 ethyl acetate: hexanes mixture to afford 120 mg of the benzyl alcohol.

EXAMPLE 11

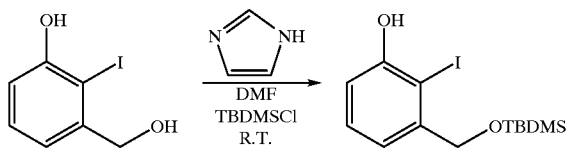

Using the analogous procedure of example 1, the carbinol was converted to the silyl ether.

$^1$H NMR (CDCl$_3$) δ: 0.10 (s, 6H), 0.95 (s, 9H), 4.70 (s, 2H), 4.94 (s, 1H), 6.68 (dd, J=2.3 Hz, 5.5 Hz, 1H), 6.83 (m, 1H), 7.16 (t, J=7.8 Hz, 1H).

EXAMPLE 12

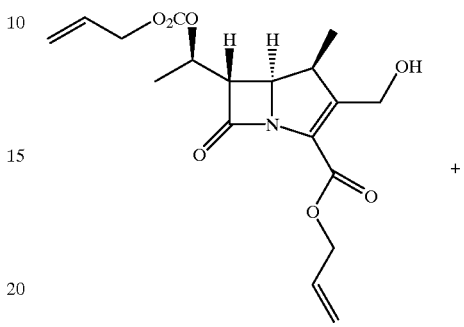

+

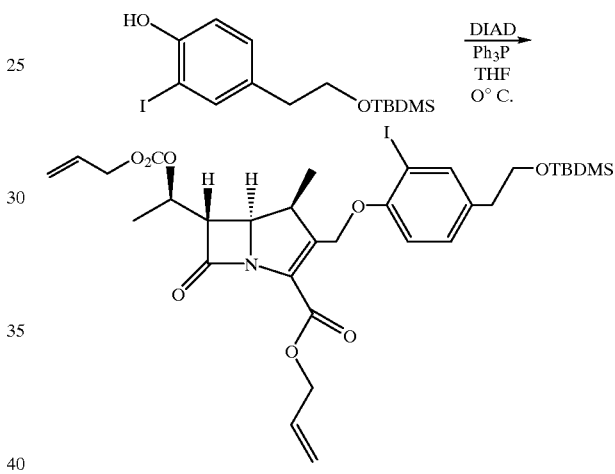

301 mg (0.824 mmoles) of bis-allyl protected carbinol, 261 mg (0.687 mmoles) of the iodophenol (Finch, H.; Pegg, N., A.; Evans, B. *Tetrahedron Lett.*, 1993, 34, 8353) and 67 mg (0.824 mmoles) triphenylphosphine were combined and was placed in an $N_2$ atmosphere. The mnixture was dissolved with 2.0 ml of anhydrous THF and chilled to 0° C. To the stirred THF solution, 0.162 ml of diisopropylazodicarboxylate (0.824 mmoles) was added. The reaction was stirred for 20 min. and evaporated.

The product was purified by plate layer chromatography with a 4:1 hexanes: ethyl acetate eluent to afford 389 mg of the silyl ether.

$^1$H NMR (CDCl$_3$) δ: 0.1 (s, 6H), 0.9 (s,9H), 1.27 (d, J=7.3 Hz, 3H), 1.45 (d, J=6.5 Hz, 3H), 2.68–2.73 (t, J=6.6 Hz, 2H), 3.44 (dd, J=3 Hz, 5 Hz, 1H), 3.62 (m, 1H), 3.72–3.78 (t, J=4.1 Hz, 2H), 4.18 (dd, J=3 Hz, 7 Hz, 1H), 4.61–4.83 (m, 5H), 5.11–5.26 (m, 1H), 5.3–5.54 (m, 5H), 5.89–6.02 (m, 2H), 6.71 (d, J=8.3 Hz, 1H), 7.12 (dd, J=2.1 Hz, 1.9 Hz, 1H), 7.63 (d, J=1.9 Hz, 1H)

EXAMPLE 13

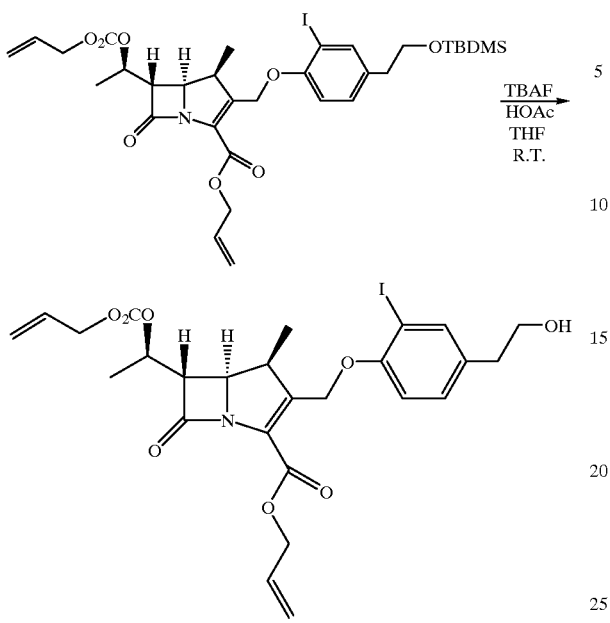

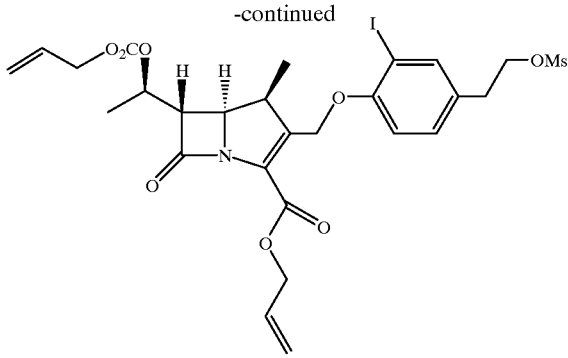

389 mg (0.536 inmoles) of the silyl ether was dissolved with 4.0 ml of anhydrous ThF, chilled to 0° C. and placed in a N₂ atmosphere. To the stirred THF solution, 0.121 ml (2.140 mmoles) of glacial acetic acid was added immediately followed by 1.287 ml (1.069 mmoles) of a 1.0 M THF solution of tetra-butylammonium fluoride. The cooling bath was removed and the reaction was stirred for 6 hrs at ambient temperature.

The reaction mixture was extracted with ethyl acetate and partitioned with H₂O-sodium bicarbonate and sat. brine. The ethyl acetate extract was dried with anhydrous sodium sulfate and concentrated in vacuo to provide a viscous oil.

The compound was purified via flash chrom. (230–400 mesh silica gel) and eluted with a 1:1 mixture of hexanes: ethyl acetate to afford 227 mg of the pure carbinol.

$^1$H NMR (CDCl₃) δ: 1.27 (d, J=7.3 Hz, 3H), 1.45 (d, J=6.5 Hz, 3H), 2.74–2.78 (t, J=6.6 Hz, 2H), 3.44 (dd, J=3 Hz, 5 Hz, 1H), 3.62 (m, 1H), 3.78–3.83 (t, J=6.5 Hz, 2H), 4.18 (dd, J=3 Hz, 7 Hz, 1H), 4.61–4.83 (m, 5H), 5.11–5.26 (m, 1H), 5.3–5.54 (m, 5H), 5.89–6.02 (m, 2H), 6.73 (d, J=8.5 Hz, 1H), 7.12 (dd, J=2.1 Hz, 6.2 Hz, 1H), 7.65 (d, J=1.9 Hz, 1H)

EXAMPLE 14

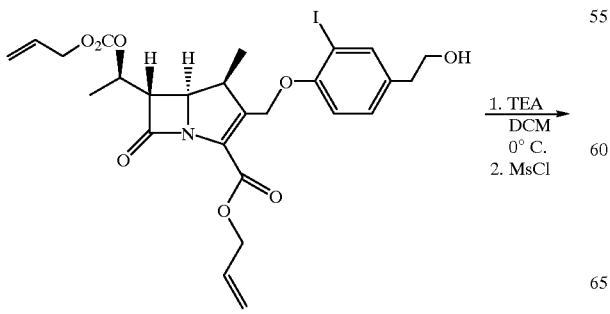

227 mg (0.370 mmoles) of carbinol was dissolved in 2.0 ml of sieve dried dichloromethane and was chilled to 0° C. and was placed under an N₂ atmosphere. To the dichloromethane solution, 0.098 ml (0.704 mmoles) of triethylamine was added and the reaction was stirred for 5 min. 0.046 ml (0.592 mmoles) of neat mesylchloride was added and the reaction was stirred for 1 hr.

The reaction mixture was extracted with ethyl acetate and partitioned with dilute aq. hydrochloric acid-ice, aq. sodium bicarbonate and saturated brine. The ethyl acetate extract was dried with anhydrous sodium sulfate and conc. in vacuo to give 205 mg of crude mesylate.

$^1$H NMR (CDCl₃) δ: 1.29 (d, J=7.3 Hz, 3H), 1.48 (d, J=6.5 Hz, 3H), 2.89–2.94 (t, J=6.6 Hz, 2H), 2.95 (s, 3H), 3.44 (dd, J=3 Hz, 5 Hz, 1H), 3.62 (m, 1H), 4.35–4.39 (t, J=6.5 Hz, 2H), 4.18 (dd, J=3 Hz, 7 Hz, 1H), 4.61–4.83 (m, 5H), 5.11–5.26 (m, 1H), 5.3–5.54 (m, 5H), 5.89–6.02 (m, 2H), 6.73 (d, J=8.5 Hz, 1H), 7.14 (dd, J=2.1 Hz, 5.9 Hz, 1H), 7.67 (d, J=1.9 Hz, 1H)

EXAMPLE 15

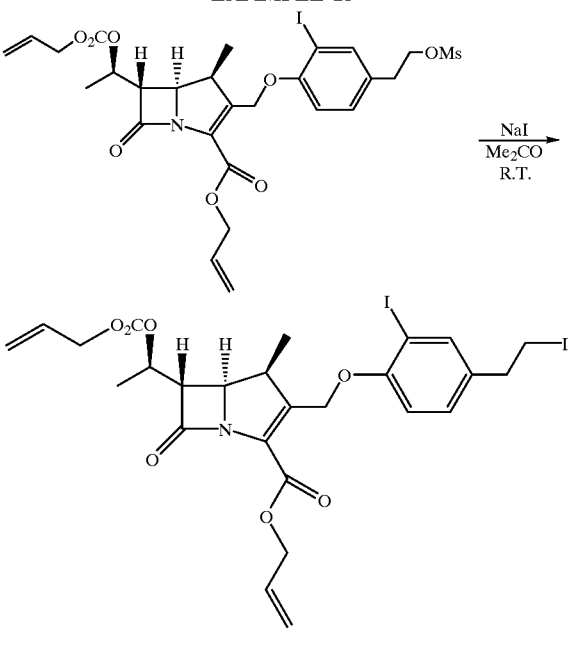

205 mg (0.296 mmoles) of the crude mesylate was ssolved in 2.0 ml of acetone and was placed in an N₂ atmosphere. To the acetone solution, 222 mg (1.481 imnoles) of sodium iodide was added and the reaction was stirred for 42 hrs. at ambient temperature.

The mixture was extracted with ethyl acetate and partitioned between dilute aq. sodium thiosulfate-ice, H₂O and saturated brine. The ethyl acetate extract was dried with anhydrous sodium sulfate and conc. in vacuo to afford 202 mg of the alkyliodide.

$^1$H NMR (CDCl$_3$) δ: 1.25 (d, J=7.3 Hz, 3H), 1.43 (d, J=6.5 Hz, 3H), 3.03–3.07 (t, J=6.9 Hz, 2H), 3.44 (dd, J=3 Hz, 5 Hz, 1H), 3.62 (m, 1H), 3.25–3.29 (t, J=7.8 Hz, 2H), 4.18 (dd, J=3 Hz, 7 Hz, 1H), 4.61–4.83 (m, 5H), 5.11–5.26 (m, 1H), 5.3–5.54 (m, 5H), 5.89–6.02 (m, 2H), 6.73 (d, J=8.5 Hz, 1H), 7.07 (dd, J=2.0 Hz, 6.1 Hz, 1H), 7.58 (d, J=1.9 Hz, 1H)

EXAMPLE 16

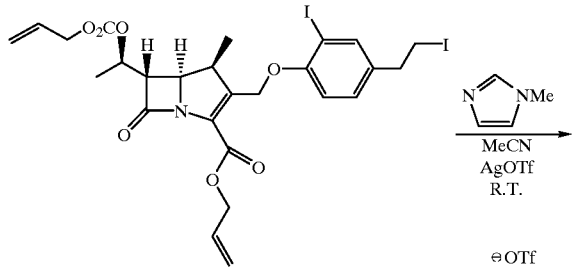

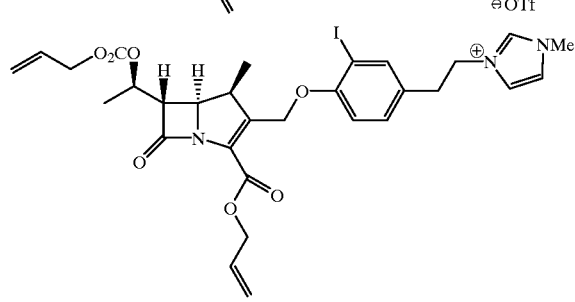

50 mg (0.069 mmoles) of the alkyliodide was dissolved with 1.0 ml of sieve dried acetonitrile and was placed in an N$_2$ atmosphere. To the stirred acetonitile solution, 0.011 ml (0.138 mmoles) of neat N-methylimidazole was added, immediately followed by the addition of 0.069 ml (0.0691 mmoles) of a 1.0 M solution of AgOTf in acetonitrile. Upon addition of the AgOTf solution, a yellow solid formed. The reaction was stirred for 24 hrs. at ambient temperature and for 2 hrs. at 50° C.

The reaction mixture was filtered through a celite pad and conc. in vacuo to a volume of ca. 1.0 ml. and was diluted with 9.0 ml of diethylether, forming a white suspension.

The etheral suspension was centrifuged and the resulting supernatant was discarded. The remaining white solid was dried in vacuo to give 32 mg of the imidazolium salt.

EXAMPLE 17

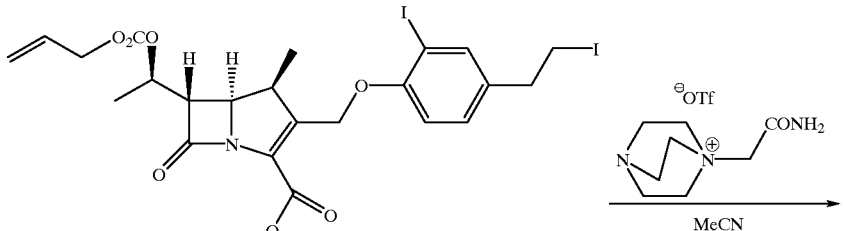

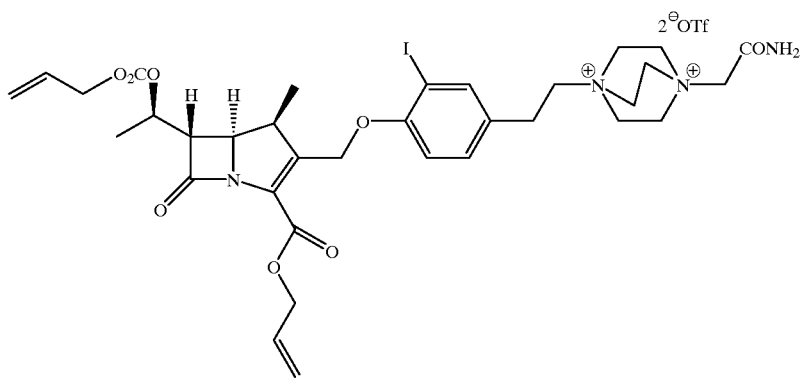

157 mg (0.216 mmoles) of the alkyliodide was combined with 69 mg (0.216 mmoles) of the dabco acetamide triflate salt and 2.0 ml of sieve dried acetonitrile in an N₂ atmosphere. To the acetonitrile solution, 0.216 ml (0.216 mmoles) a 1.0 M solution of AgOTf in acetonitrile was added. Upon the addition of the AgOTf solution, a yellow ppt. formed. The reaction was stirred for 24 hrs. at R.T.

The reaction mixture was filter through a celite pad and was conc. in vacuo to ca. 2.0 ml and was diluted with 8.0 ml of diethylether forming a suspension.

The etheral suspension was centrifuged and the resulting supernatant was discarded. The remaining off-white solid was dried in vacuo to afford 120 mg of the salt.

EXAMPLE 18

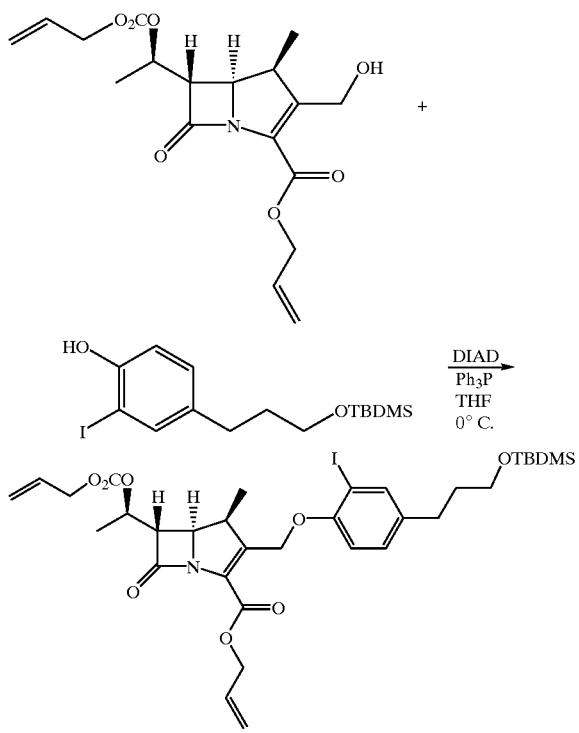

Using the analogous procedure of example 12, the bis-allyl protected carbinol was converted to the silyl ether.

¹H NMR (CDCl₃) δ: 0.048 (s, 6H), 0.90 (s,9H), 1.28 (d, J=6.2 Hz, 3H), 1.45 (d, J=6.3 Hz, 3H), 1.75 (m, 2H), 2.56 (t, J=8.9 Hz, 2H), 3.44 (dd, J=2.9 Hz, 6 Hz, 1H), 3.60 (m, 3H), 4.19 (dd, J=3.0 Hz, 7.0 Hz, 1H), 4.60 (m, 2H), 4.63–4.87 (m, 3H), 5.11 (m., 1H), 5.26–5.54 (m, 5H), 5.89–6.02 (m, 2H), 6.71 (d, J=8.4 Hz, 1H), 7.07 (dd, J=2.2 Hz, 6.2 Hz, 1H), 7.60 (d, J=2.1Hz, 1H)

EXAMPLE 19

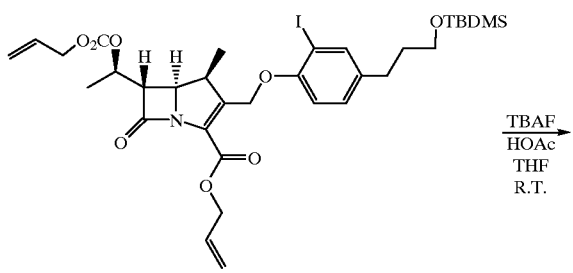

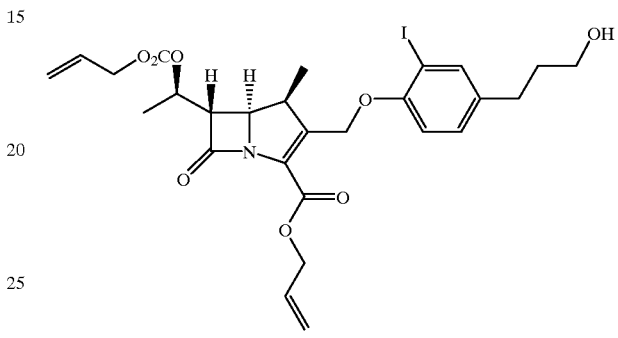

Using the analogous procedure of example 13, the silyl ether was converted to the carbinol.

¹H NMR (CDCl₃) δ: 1.27 (d, J=7.4 Hz, 3H), 1.45 (d, J=6.3 Hz, 3H), 1.81 (m, 2H), 2.59 (t, J=8.9 Hz, 2H), 3.44 (dd, J=3.0 Hz, 4.9 Hz, 1H), 3.57 (m, 3H), 4.19 (dd, J=3.1 Hz, 6.9 Hz, 1H), 4.61 (m, 2H), 4.68–4.87 (m, 3H), 5.11 (m, 1H), 5.26–5.54 (m, 5H), 5.89–6.02 (m, 2H), 6.72 (d, J=8.4 Hz, 1H), 7.09 (dd, J=2.0 Hz, 6.3 Hz, 1H), 7.62 (d, J=2.0 Hz, 1H)

EXAMPLE 20

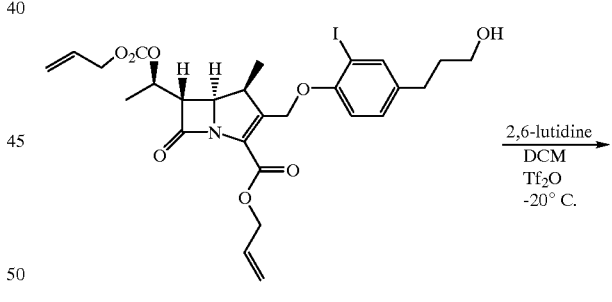

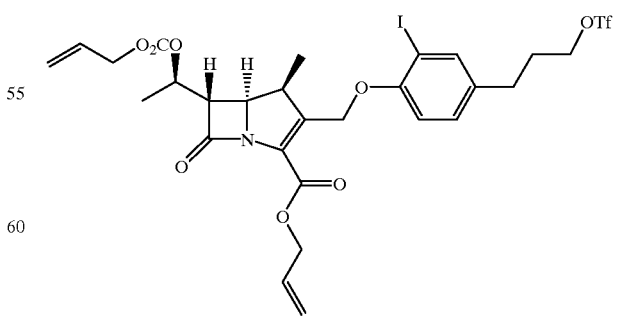

131 mg (0.209 mmoles) of the carbinol was dissolved in 1 ml of sieve dried dichloromethane and chilled to −20° C.

and was placed in an N₂ atmosphere. To the stirred solution, 0.026 ml (0.220 mmoles) of 2,6-lutidine was added and the reaction was stirred for 5 min. 0.038 ml (0.231 mmoles) of triflic anhydride was then added and the reaction was stirred for an additional 20 min.

The reaction was then extracted with ethyl acetate and partitioned with dilute aq. hydrochloric acid-ice, H₂O and saturated brine. The ethyl acetate extract was then dried with anhydrous sodium sulfate and conc. in vacuo to provide 121 mg of the alkyl triflate.

EXAMPLE 21

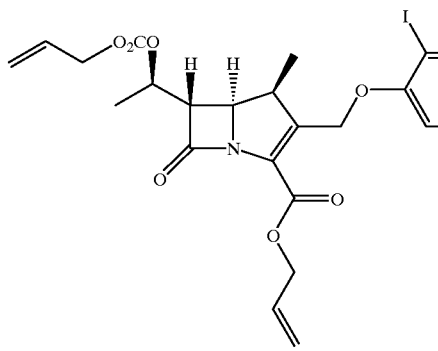

121 mg (0.160 mmoles) of the triflate was combined with the dabco acetamide triflate salt and dissolved in 2.0 ml of acetonitrile and was placed in an N₂ atmosphere. The reaction was stirred for 1 hr. at ambient temperature.

The reaction mixture was filtered through a celite pad and conc. in vacuo to a volume of ca. 1.0 ml. and was diluted with 9.0 ml of diethylether, forming a white suspension.

The ethereal suspension was centrifuged and the resulting supernatant was discarded. The remaining off-white solid was dried in vacuo to give 137 mg of salt.

EXAMPLE 22

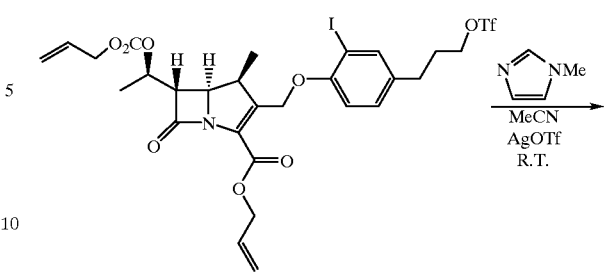

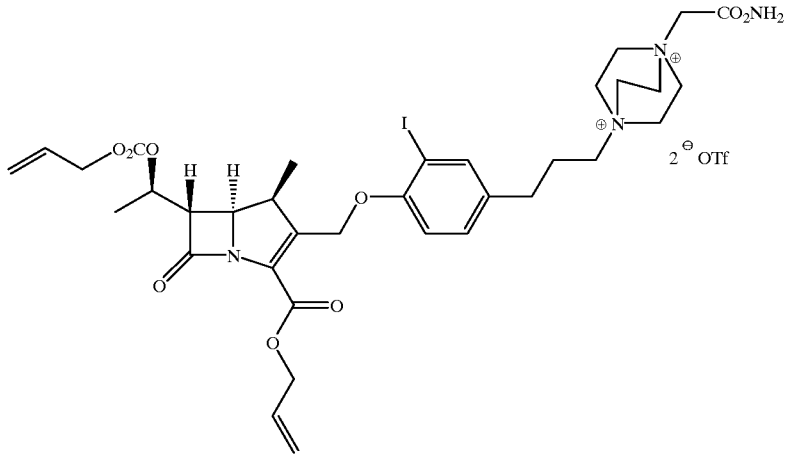

-continued

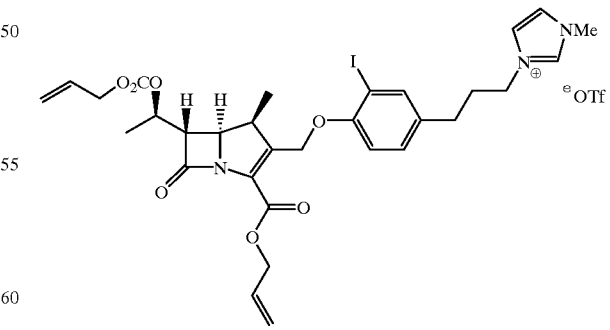

37 mg (0.0781 mmoles) of the alkyl triflate was combined with 0.0053 ml (0.0664 mmoles) of N-methylimidazole and dissolved in 2.0 ml of acetonitrile and was placed in an N₂ atmosphere. The reaction was stirred for 1 hr. at ambient temperature.

The reaction mixture was filtered through a celite pad and conc. in vacuo to a volume of ca. 1.0 ml. and was diluted with 9.0 ml of diethylether, forming a white suspension.

The etheral suspension was centrifuged and the resulting supernatant discarded. The remaining off-white solid was dried in vacuo to give 62 mg of the imidazolium salt.

EXAMPLE 23

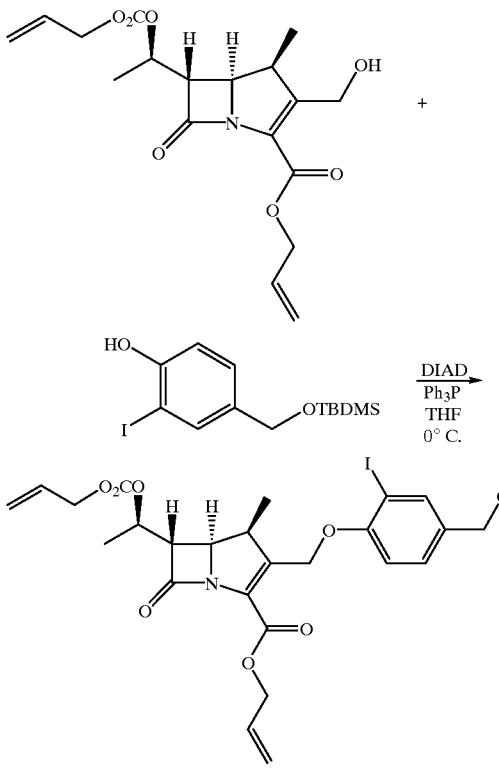

Using the analogous procedure of example 12, the bis-allyl protected carbinol was converted to the silyl ether.

$^1$H NMR (CDCl$_3$) δ: 0.092 (s, 6H), 0.93 (s,9H), 1.27 (d, J=7.5 Hz, 3H), 1.45 (d, J=6.3 Hz, 3H), 3.44 (dd, J=2.9 Hz, 5 Hz, 1H), 3.56 (m, 1H), 4.19 (dd, J=3 Hz, 7 Hz, 1H), 4.61–4.64 (m, 4H), 4.69–4.87 (m, 3H), 5.11 (m, 1H), 5.26–5.56 (m, 1H), 5.87–6.02 (m, 2H), 6.76 (d, J=7.4 Hz, 1H), 7.21 (dd, J=2.0 Hz, 6.4, 1H), 7.73 (d, J=2.1 Hz, 1H).

EXAMPLE 24

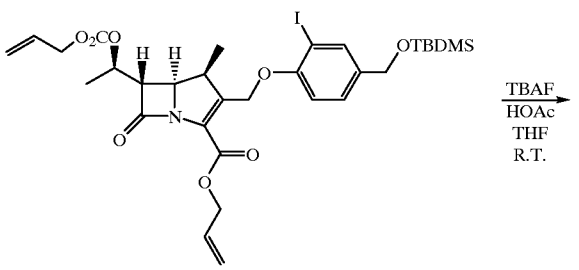

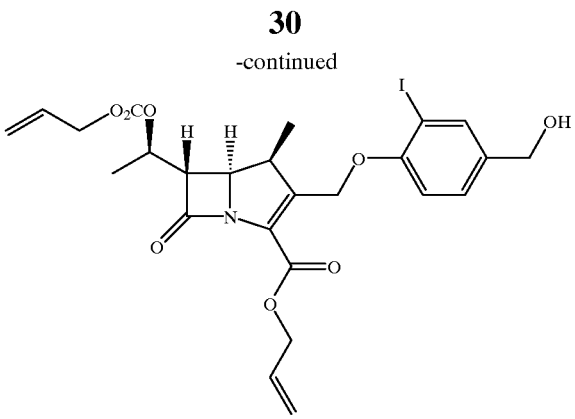

Using the analogous procedure of example 13, the silyl ether was converted to the benzyl alcohol.

$^1$H NMR (CDCl$_3$) δ: 1.27 (d, J=7.4 Hz, 3H), 1.45 (d, J=6.4 Hz, 3H), 3.41 (dd, J=3.1 Hz, 5 Hz, 1H), 3.55 (m, 1H), 4.17 (dd, J=3 Hz, 7 Hz, 1H), 4.56 (d, J=5.4 Hz, 2H), 4.59–4.62 (m, 2H), 4.67–4.84 (m, 3H), 5.09 (m, 1H), 5.24–5.54 (m, 5H), 5.58–6.0 (m, 2H), 6.72(d, J=8.4 Hz, 1H), 7.24 (dd, J=2.2 Hz, 6.2, 1H), 7.77 (d, J=2.1 Hz, 1H).

EXAMPLE 25

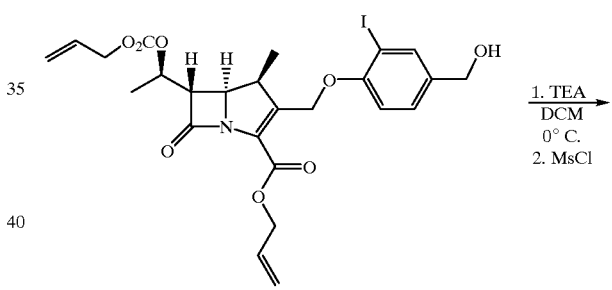

Using the analogous procedure of example 14, the benzyl alcohol was converted to the mesylate.

$^1$H NMR (CDCl$_3$) δ: 1.27 (d, J=7.4 Hz, 3H), 1.45 (d, J=6.4 Hz, 3H), 2.96 (s, 3H), 3.45 (dd, J=3.0 Hz, 5 Hz, 1H), 4.20 (m, 1H), 4.61 (m, 2H), 4.63–4.85 (m, 3H), 5.13 (s, 2H), 5.26–5.59 (m, 5H), 5.89–6.0 (m, 2H), 6.82 (d, J=8.4 Hz, 1H), 7.34 (dd, J=2.2 Hz, 7.2, 1H), 7.85 (d, J=2.1 Hz, 1H).

EXAMPLE 26

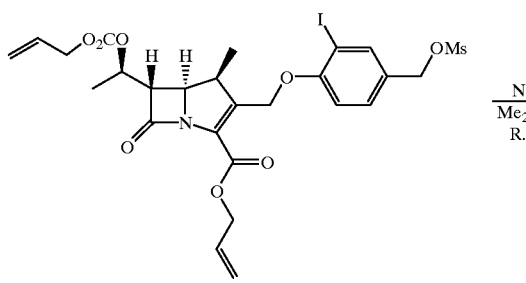

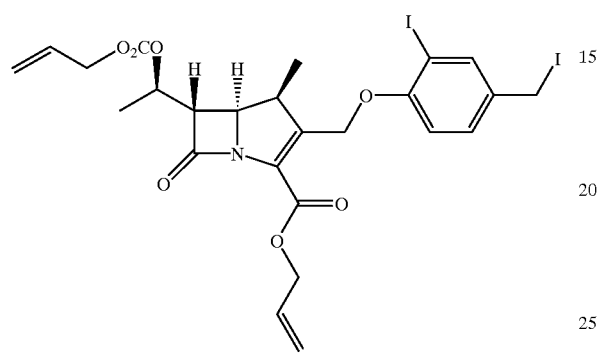

Using thie analogous procedure of example 15, thie mesylate was converted to thie benzyl iodide.

$^1$H NMR (CDCl$_3$) δ: 1.26 (d, J=7.4 Hz, 3H), 1.45 (d, J=6.4 Hz, 3H), 3.45 (dd, J=3.2 Hz, 4.9 Hz, 1H), 3.59 (m, 1H), 4.20 (dd, J=3.9 Hz, 7.1 Hz, 1H), 4.38 (s, 2H), 4.61–4.68 (m, 2H), 4.68–4.87 (m, 3H), 5.11(m, 1H), 5.26–5.55 (m, 5H), 5.87–6.02 (m, 2H), 6.71 (d, J=8.5 Hz, 1H), 7.29 (dd, J=2.3 Hz, 6.21, 1H), 7.79 (d, J=2.2 Hz, 1H).

EXAMPLE 27

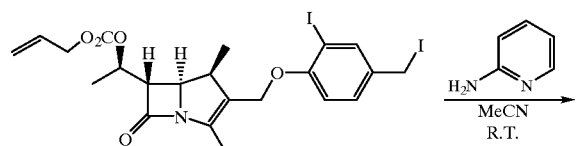

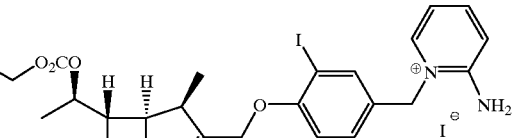

25 mg (0.0353 mmoles) of the benzyl iodide was dissolved with 1.0 ml of sieve dried acetonitrile and was placed in an N$_2$ atmosphere. To the stirred acetonitrile solution, 6.6 mg (0.0707 mmoles) of 2-aminopyridine was added and the reaction was stirred for 18 hrs. at ambient temperature.

The reaction mixture was diluted with 9.0 ml of diethylether forming an oily suspension.

The etheral suspension was centrifuged and the resulting supernatant was discarded. The remaining oil was dried in vacuo to give 32 mg of the pyridinium salt.

EXAMPLE 28

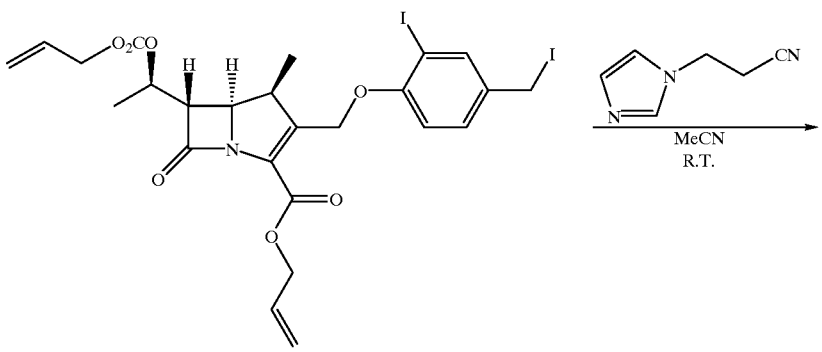

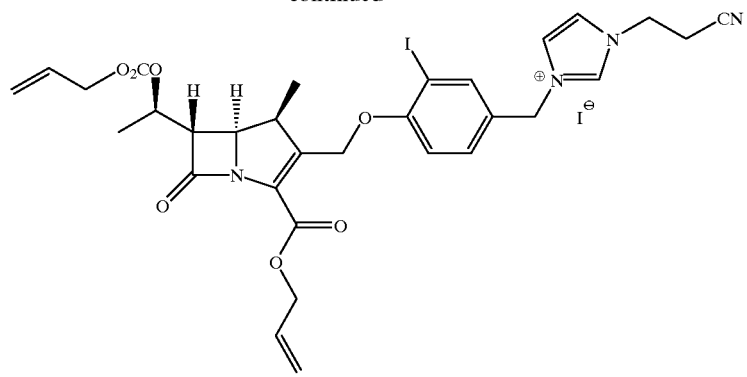

3 mg (0.042 mmoles) of the benzyl iodide was dissolved with 2.0 ml of sieve dried acetonitrile and was placed in an $N_2$ atmosphere. To the stirred acetonitrile solution, 0.007 ml (0.085 mmoles) of neat N-cyanoethylimidazole was added to the reaction and was stirred for 18 hrs. at ambient temperature. The reaction mixture was conc. in vacuo to ca. 1.0 ml and was diluted with 9.0 ml of diethylether forming an oily precipitate.

The etheral mixture was centnfged and the resulting supernatant discarded. The remaining oil was dried in vacuo to give 26 mg of the imidazolium salt.

EXAMPLE 29

137 mg (0.127 mmoles) of the bis-allyl protected dabco salt was dissolved in 3.0 ml of sieved dried DMF and placed in an $N_2$ atmosphere. To the stirred DMF solution, 29 mg (0.025 mmoles) of $Pd(Ph_3P)_4$ and 20 mg (0.076 mmoles) of $Ph_3P$ were combined and added in one portion forming a suspension. 0.020 ml (0.140 mmoles) of neat 2-ethylhexanoic acid was added followed by the addition of 0.283 ml (0.140 mmoles) of a 0.5 M solution of sodium-2-ethylhexanoate in ethyl acetate.

The reaction was stirred for 5 min. at ambient temperature, at which time a homogeneous solution was obtained. The reaction was chilled to 0° C. and stirred for an additional 1.5 hrs.

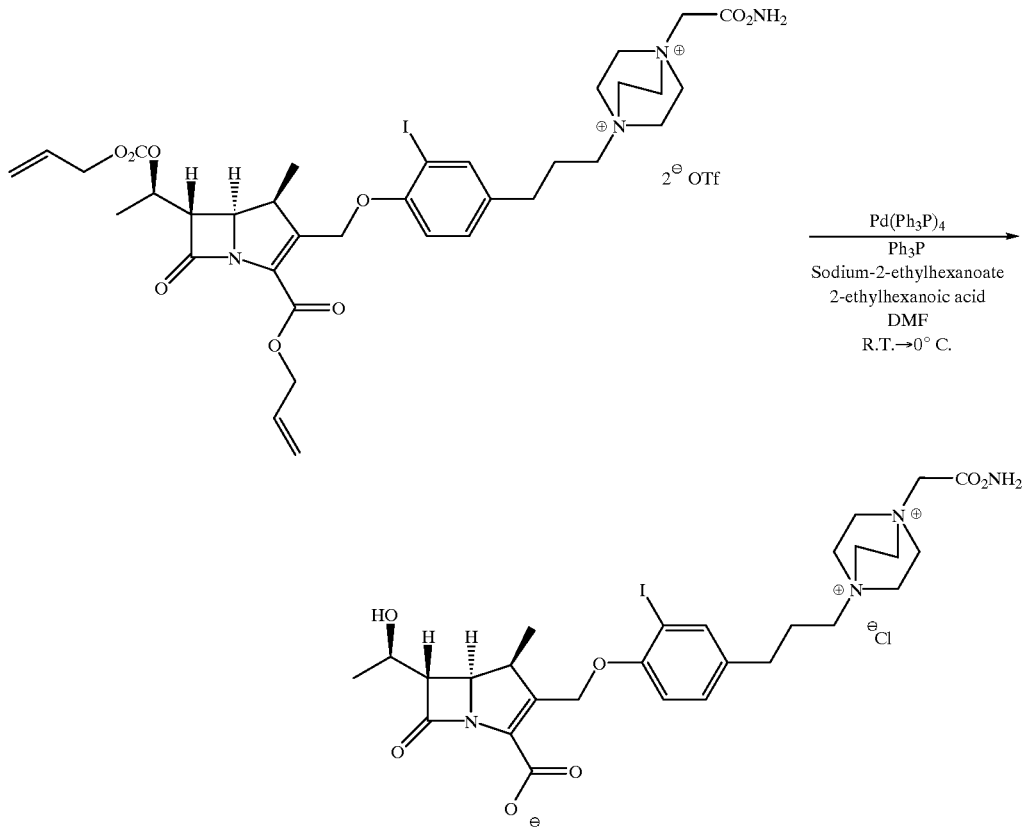

The reaction was then diluted with 10.0 ml of diethylether forming a suspension. The etheral mixture was centrifuged and the resulting supernatant was discarded. The resulting deblocked carbapenem was washed twice with diethylether and dried in vacuo which gave 116 mg of an amorphous solid.

The dried solid was then dissolved in 5 ml of 5% aq. brine and was chromatogaphed on 2.0 ml's of MacroPrep ion exchange resin and eluted with 100 ml of 5% aq. brine. The 5% aq. brine effluent containing the purified carbapenem was desalted on 15 ml's of Amberchrom CG-161 resin using an $H_2O$-aq. acetonitrile gradient elution.

The resulting aq. fractions which contained the purified carbapenem were combined and lyophilized to give 33 mg of the desired carbapenem as a white lyophilizate.

$^1$H NMR ($D_2O$) δ: 1.49 (d, J=6.9 Hz, 3H), 1.53 (d, J=6.5 Hz, 3H), 2.33 (m, 2H), 2.89 (m, 2H), 3.67 (m, 2H) 3.79–3.83 (m, 2H), 4.23 (bs, 6H), 4.39 (dd, J=3 Hz, 7 Hz, 1H), 4.49 (bs, 6H) 4.63 (m, 1 H), 5.01 (d, J=13.7 Hz, 1H), 5.85 (d, J=9.2 Hz, 1H), 7.27 (d, J=8.5 Hz, 1H), 7.56 (dd, J=2.0 Hz, 6.4 Hz, 1H), 8.02 (d, J=2.1 Hz, 1H)

EXAMPLE 30

26 mg (0.0314 mmoles) of the bis-allyl protected imidazolium salt was dissolved with 1.0 ml of a 1:1 mixture of dichloromethane and ethyl acetate and was placed in an $N_2$ atmosphere. To the stirred solution, 7.3 mg (0.0063 mmoles) of Pd($Ph_3P)_4$ and 5 mg (0.019 mmoles) of $Ph_3P$ were combined and added in one portion forming a suspension. 0.0048 ml (0.0345 mmoles) of neat 2-ethylhexanoic acid was added followed the addition of 0.069 ml (0.0345 mmoles) of a 0.5 M solution of sodium-2-ethylhexanoate in ethyl acetate.

The reation was stirred for 5 min. at ambient temperature and was chilled to 0° C. and stirred further for an additional 1.5 hrs.

The reaction mixture was then diluted with 8.0 ml of diethylether forming a white suspension. The etheral mixture was centrifuged and the resulting supernatant was discarded. The resulting deblocked carbapenem was washed twice with diethylether and dried in vacuo to give 11 mg of an amorphous solid.

The crude product was purified with reverse phase plate layer chromatography in a 4:1 mixture of $H_2O$: acetonitrile to afford 6.7 mg of desired carbapenem as a white lyophilizate.

$^1$H NMR ($D_2O$) δ: 1.52 (d, J=7.4 Hz, 3H), 1.56 (d, J=6.2 Hz, 3H), 3.43 (t, J=2.5 Hz, 2H), 3.68 (m, 2H), 4.42–4.45 (dd, J=3 Hz, 7.3 Hz, 1H), 4.49 (m, 1H), 4.82 (t, J=4.1 Hz, 2H), 5.11 (d, J=7.7 Hz, 1H), 5.63 (s, 2H), 5.92 (d, J=5.9 Hz, 1H), 7.40 (d, J=5.4 Hz, 1H), 7.78 (d, J=9.5 Hz, 1H), 7.85 (d, J=1.8 Hz, 1H), 7.93 (d, 1.8 Hz, 1H), 8.21 (d, J=2.1 Hz, 1H).

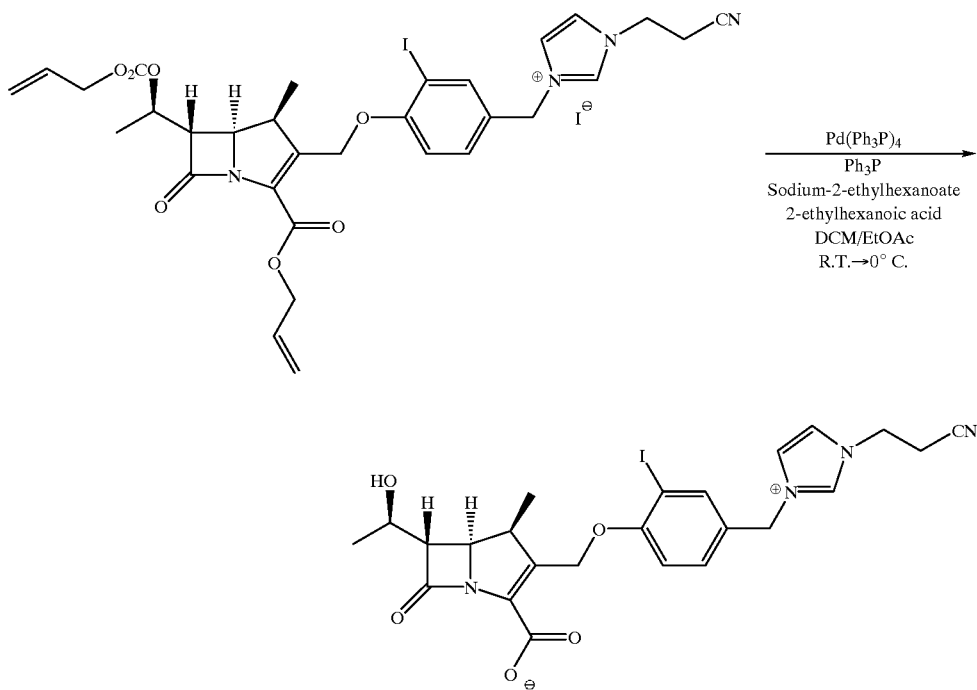

EXAMPLE 31
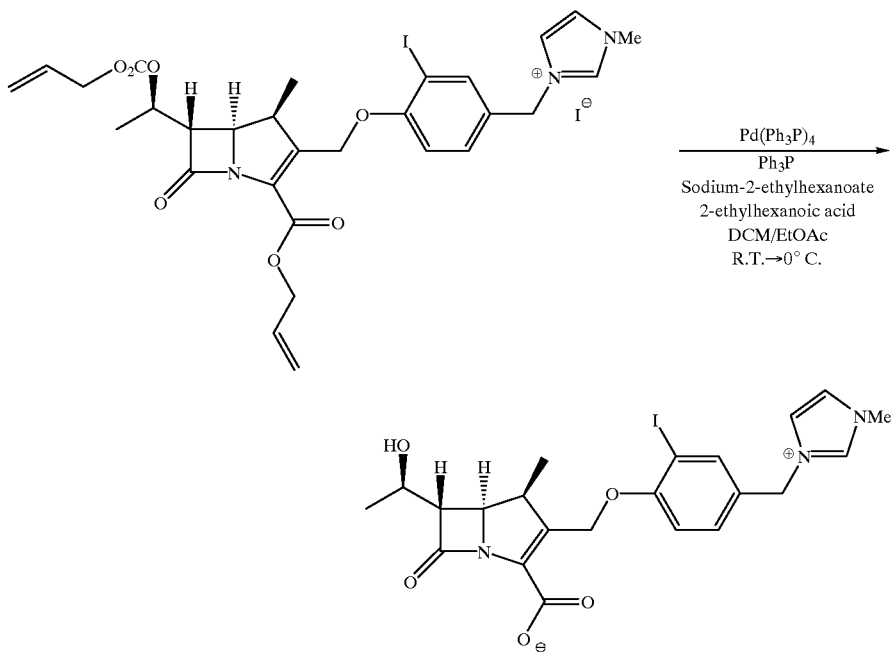
Using the analogous procedure from example 30, the bis-allyl protected imidazolim salt was deblocked to give the desired carbapenem.
$^1$H NMR (D$_2$O) δ: 1.54 (d, J=6.7 Hz, 3H), 1.57 (d, J=5.4 Hz, 3H), 3.69 (m, 2H), 4.18 (s, 3H), 4.43 (d, J=3 Hz, 10.1 Hz, 1H), 4.5 (m, 1H), 5.12 (d, J=13.1 Hz, 1H), 5.58 (s, 2H), 5.93 (d, J=13.9 Hz, 2H), 7.39 (dd, J=4.9 Hz, 2.2 HZ, 1H), 7.40 (d, J=5.4 Hz, 1H), 7.59–7.79 (m, 3H), 8.21 (s, 1H).
EXAMPLE 32
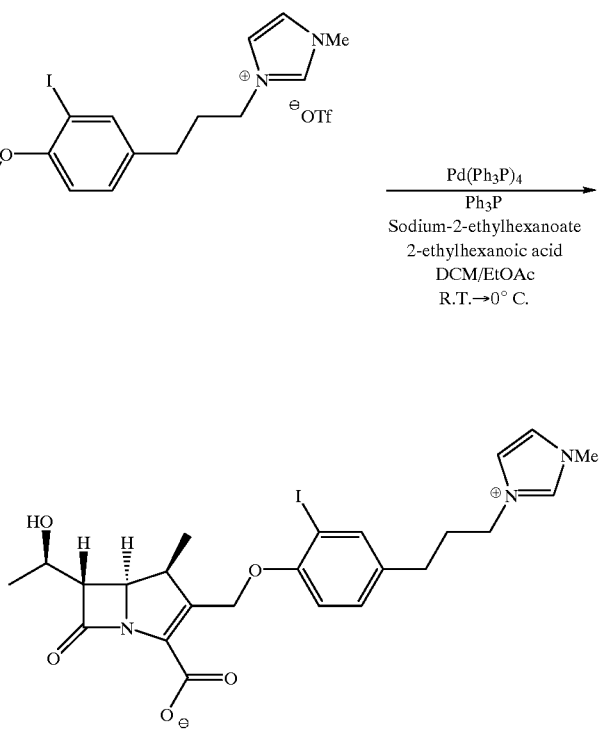

Using the analogous procedure of example 30, the imidazolium product was obtained.

1H NMR (D$_2$O) δ: 1.38 (dd, J=6.1 Hz, 3H), 1.43 (dd, J=6.1 Hz, 3H), 2.34 (m, 2H), 2.78 (m, 2H), 3.57 (m, 2H), 3.99 (s, 3H), 4.29–4.37(dd, J=2.8 Hz, 7.1 Hz, 1H), 4.40 (m, 2H), 4.93 (d, J=14.1, Hz, 1H), 5.39 (d, J=14.1 Hz, 1H), 7.12 (d, J=4.4 Hz, 1H), 7.37 (d, J=8.0 Hz, 1H), 7.55 (s, 1H), 7.58(s, 1H), 7.58(s, 1H), 7.80(s, 1H), 8.74(s, 1H)

EXAMPLE 33

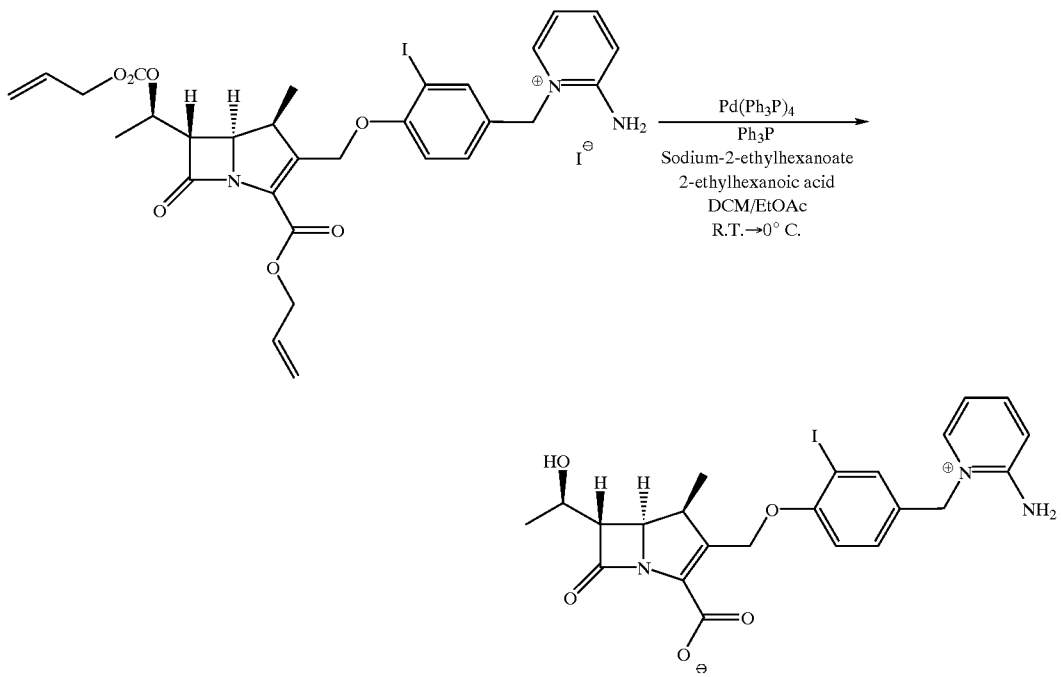

Using the analogous procedure of example 30, the bis-allyl protected pyridinium salt was deblocked to give the desired carbapenem.

$^1$H NMR (D$_2$O) δ: 1.54 (d, J=6.1 Hz, 3H), 1.57 (d, J=5.4 Hz, 3H), 3.69 (m, 2H), 4.43 (d, J=3 Hz, 10.1 Hz, 1H), 4.5 (m, 1H), 5.12 (d, J=13.1 Hz, 1H), 5.58 (s, 2H), 5.93 (d, J=13.9 Hz, 2H), 7.27 (t, J=8.7Hz, 3.2 Hz, 1H), 7.40 (d, J=8.1, Hz, 1H), 7.61 (d, J=8.7 Hz, 1H3, 7.98 (d, J=2.3 Hz, 1H), 8.15 (s, 1H), 8.20 (m, 2H).

EXAMPLE 34

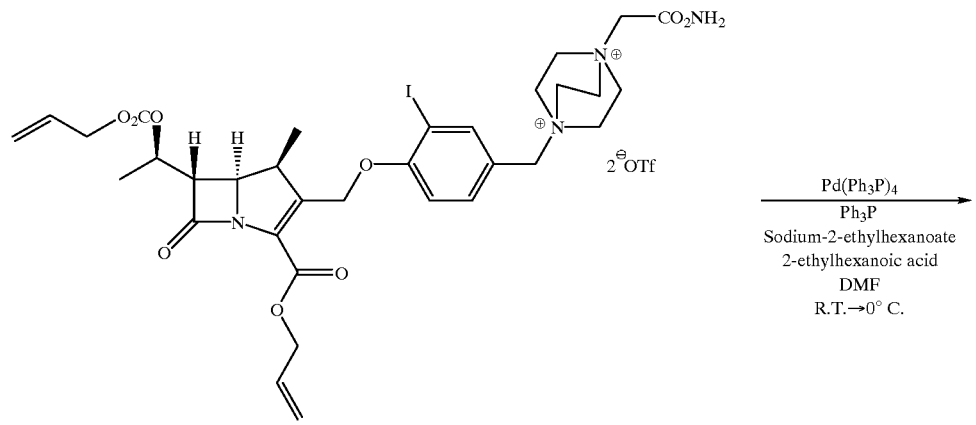

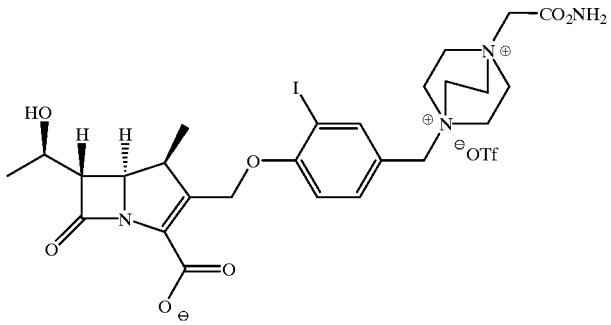

35 mg (0.0334 mmoles) of the bis-allyl protected dabco salt was dissolved in 3.0 ml of sieved dried DMF and was placed in an $N_2$ atmosphere. To the stirred DMF solution, 7.7 mg (0.0067 mmoles) of $Pd(Ph_3P)_4$ and 5.3 mg (0.020 mmoles) of $Ph_3P$ were combined and added in one portion forming a suspension. 0.005 ml (0.0367 mmoles) of neat 2-ethylhexanoic acid was added followed by the addition of 0.073 ml(0.0367 mmoles) of a 0.5 M solution of sodium-2-ethylhexanoate in EtOAc.

The reaction was stirred for 5 min. at ambient temperature at which time a homogeneous solution was obtained. The reaction was chilled to 0° C. and stirred for an additional 1.5 hrs.

The reaction was then diluted with 10.0 ml of diethylether forming a suspension. The etheral mixture was centrifuged and the resulting supernatant was discarded. The resulting deblocked carbapenem was washed twice with diethylether and dried in vacuo to give 8.6 mg of the compound as the triflate salt.

$^1$H NMR ($D_2O$) δ: 1.51–1.54 (m, 6H), 3.68–3.71 (m, 2H), 4.23 (s, 6H), 4.43 (m, 8H), 4.62 (s, 2H), 4.95 (s, 2H), 5.15 (d, J=13.7 Hs, 1H), 5.93 (d, J=13.7 Hz, 1H), 7.46 (d, J=8.7 Hz, 1H), 7.84 (d, J=8.7 Hz, 1H), 8.30 (s, 1H).

EXAMPLE 35

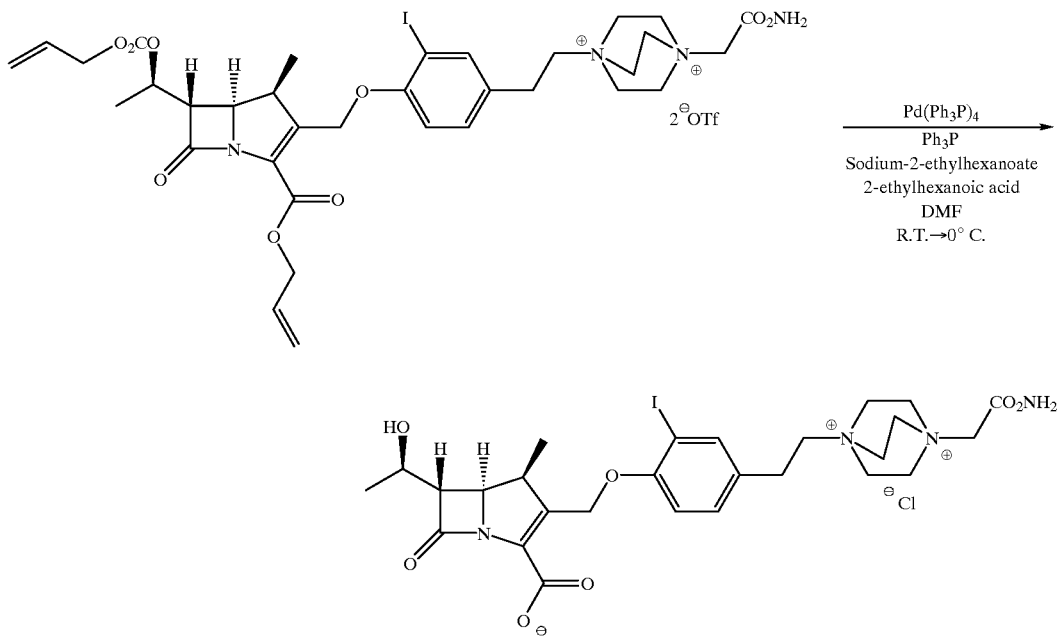

Using the analogous procedure of example 29, the bis-allyl protected dabco salt was deblocked to give the desired carbapenem.

¹H NMR (D₂O) δ: 1.49 (d, J=6.9 Hz, 3H), 1.53 (d, J=6.5 Hz, 3H), 3.37 (m, 2H) 3.66 (m, 2H), 4.03 (m, 2H), 4.31 (bs, 6H), 4.40 (d, J=10 Hz, 2H) 4.73 (m, 8H), 5.04 (d, J=13.9 Hz, 1H), 5.85 (d, J=13.0 Hz, 1H), 7.30 (dd, J=8.1 Hz, 3.2 Hz, 1H), 7.63 (d, J=8.5 Hz, 1H), 8.10 (s, 1H)

EXAMPLE 36

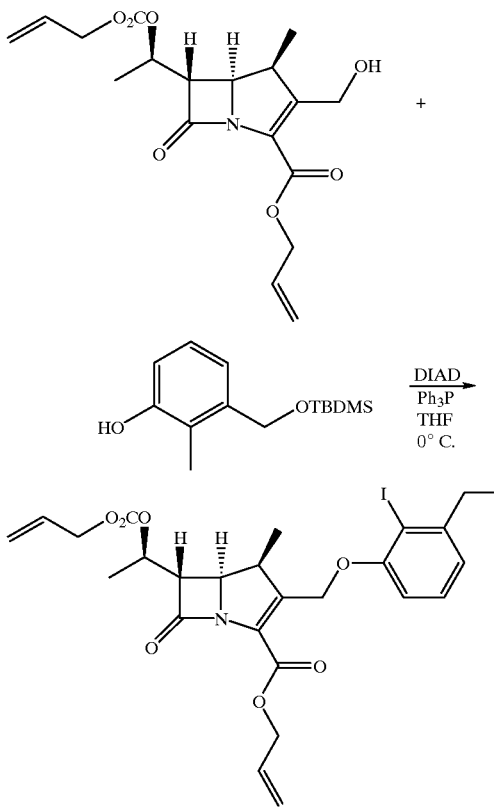

Using the analogous procedure of example 12, the bis-allyl protected carbinol was converted to the silyl ether.

¹H NMR (CDCl₃) δ: 0.09 (s, 6H), 0.93 (s,9H), 1.22 (d, J=8.3 Hz, 3H), 1.44(d, J=6.3 Hz, 3H), 3.44 (m, 2H), 4.12 (dd, J=3 Hz, 7 Hz, 1H), 4.62 (dd, J=9.2 Hz, 1.3 Hz, 2H), 4.70–4.87 (m, 5H), 5.10 (m, 1H), 5.25–5.5 (m, 5H), 5.68–6.0 (m, 2H), 6.74 (dd, J=8.2 Hz, 2.1 Hz, 1H), 6.89 (m, 1H), 7.23 (t, J=7.9 Hz, 1H)

EXAMPLE 37

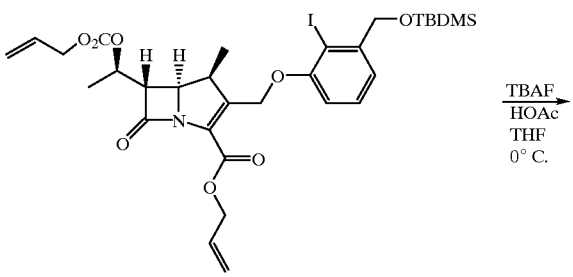

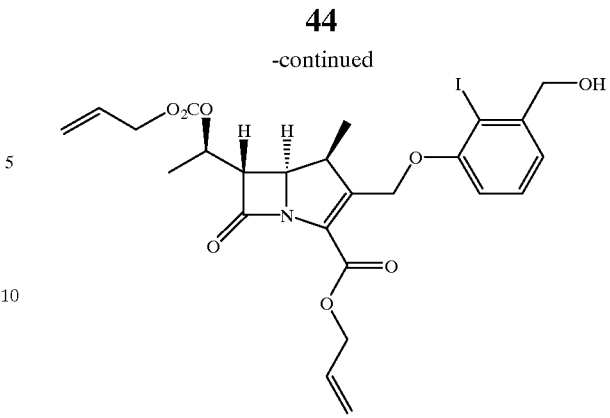

Using the analogous procedure of example 13, the silyl ether was converted to the benzyl alcohol.

¹ H NMR (CDCl₃) δ: 1.22 (d, J=8.3 Hz, 3H), 1.44(d, J=6.3 Hz, 3H), 3.44 (m, 2H), 4.15 (dd, J=3 Hz, 7 Hz, 1H), 4.59 (dd, J=7.0 Hz, 1.5 Hz, 2H), 4.64 (1)s, 2H), 4.68A4.80 (m, 3H), 5.08 (m, 1H), 5.23 (m, 5H), 5.83 (m, 2H), 6.81 (dd, J=1.4 Hz, 8 Hz, 1H), 6.93 (m, 1H), 7.23 (t, J=9 Hz, 1H).

EXAMPLE 38

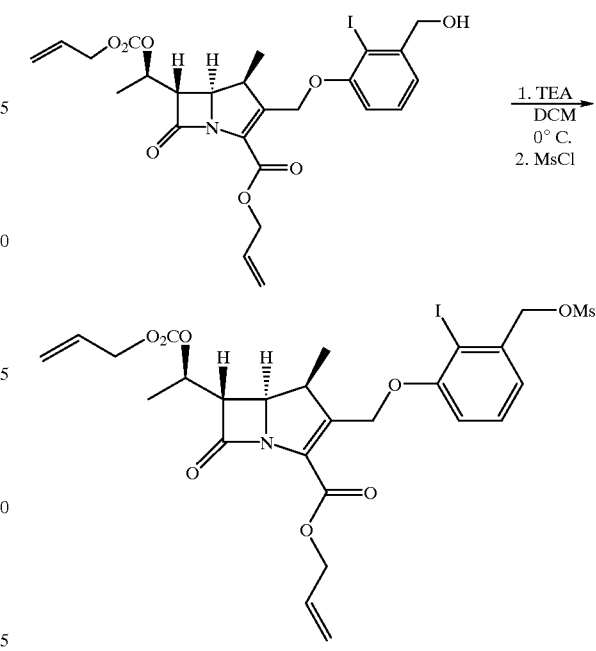

Using the analogous procedure of example 14, the benzyl alcohol was converted to the benzylic inesylate.

¹ H NMR (CDCl₃) δ: 1.22 (d, J=7.4 Hz, 3H), 1.44 (d, 3H) 14.4 Hz, 3H), 2.94 (s, 3H), 3.42 (m, 2H), 4.16 (dd, J=3.1 Hz, 6.9 Hz, 1H), 4.60 (in, 2H), 4.62 (in, 3H), 5.10 (m, 1H), 5.19 (s, 2H), 5.25 (m, 5H), 5.85–6.02 (m, 2H), 6.89 (m, 2H), 6.90 (m, 1H), 7.28 (t, J=7.9 Hz, 1H)

EXAMPLE 39

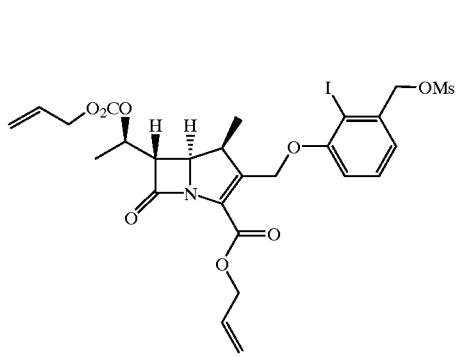

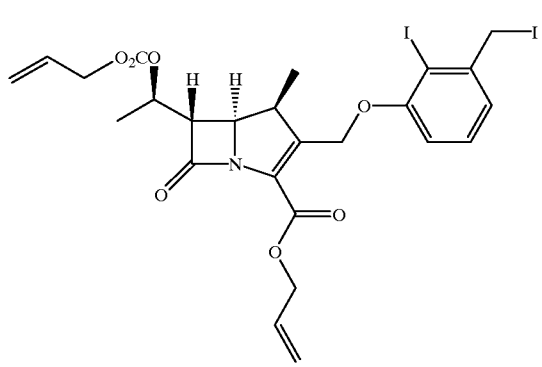

Using the analogous procedure of example 15, the benzylic mesylate was converted to benzyl iodide.

$^1$H NMR (CDCl$_3$) δ: 1.24 (d, J=5.7 Hz, 3H), 1.44 (d, J=6.3 Hz, 3H), 3.42 (m, 2H), 4.16(dd, J=3.0 Hz, 9.8 Hz, 1H), 4.39 (s, 2H) 4.60 (m, 2H), 4.71 (m, 3H), 5.10 (mn, 1H), 5.25 (in, 5H), 5.85–6.02 (m, 2H), 6.75 (dd, J=2.5 Hz, 5.5 Hz, 1H), 6.90 (m, 1H), 7.16 (t, J=8.9 Hz, 1H)

EXAMPLE 40

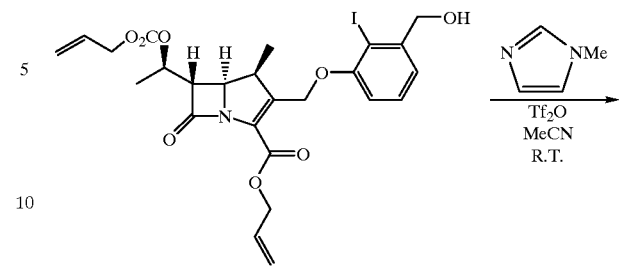

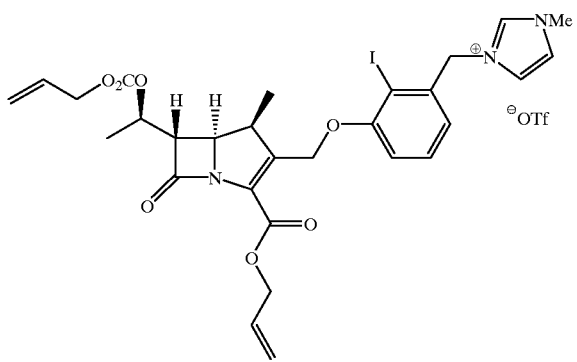

46 mg (0.0619 mmoles) of benzyl alcohol was dissolved in 1 ml of sieve dried dichioromethane and was placed in an N$_2$ atmosphere. The stirred solution, was chilled to −40° C. and 0.012 ml (0.1299 mmoles) of N-methylirnidazole was added. The solution was stirred for 5 min. and 0.0136 ml (0.0136 mmoles) of a 1.0 M solufion of AgOTf in acetonitrie was added.

The reaction mixture was diluted with 9.0 ml of diethylether, forming a white suspension.

The etheral suspension was centrfged and the resulting supernatant was discarded. The remaining off-white solid was dried in vacuo to give 24 mg of the imnidazoliurn salt.

EXAMPLE 41

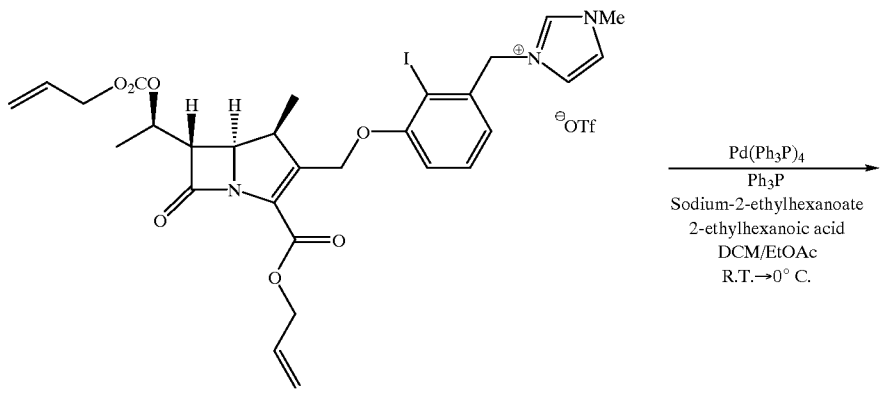

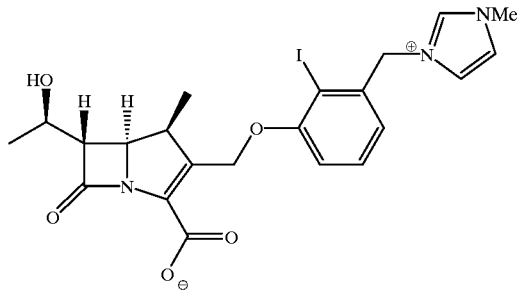
Using the analogous procedure of example 30, the bis-allyl protected imidazolium salt was deblocked to provide the desired carbapenem.
$^1$H NMR (D$_2$O) δ: 1.41 (d, J=7.3 Hz, 3H), 1.50 (d, J=6.4 Hz, 3H), 3.43 (m, 1H), 3.60 (m, 1H), 4.16 (s, 3H), 4.28 (d, J=9.6 Hz, 1H), 4.45 (m, 1H), 5.03 (d, J=14.0 Hz, 1H), 5.60 (s, 2H), 5.78 (d, J=13.9 Hz, 1H), 7.26 (s, 1H), 7.31 (m, 2H), 7.767.71 (m, 2H).
EXAMPLE 42
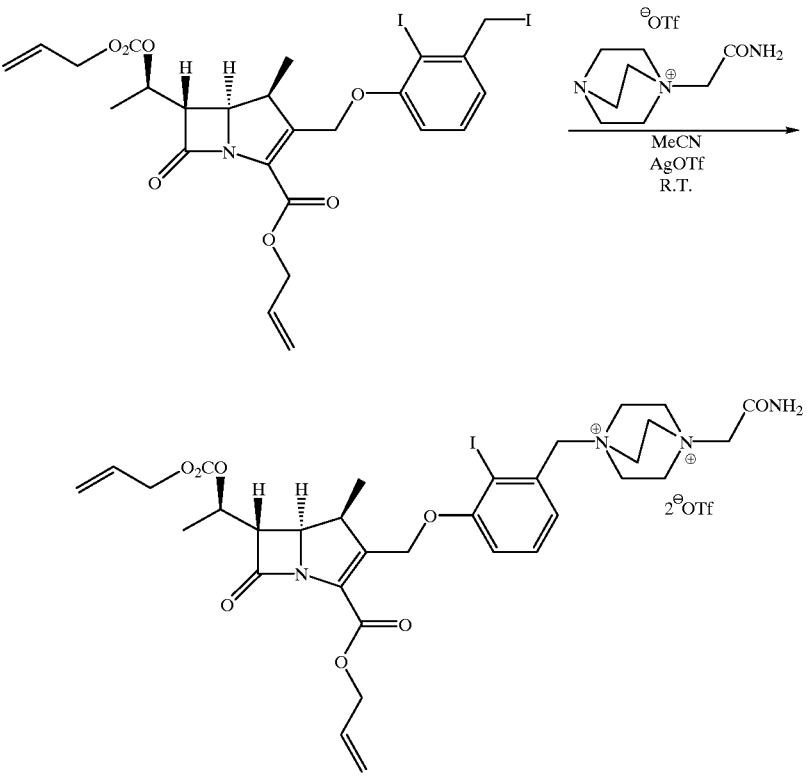
Using the analogous procedure of example 17, the benzyl iodide was converted to the triflate salt.

EXAMPLE 43

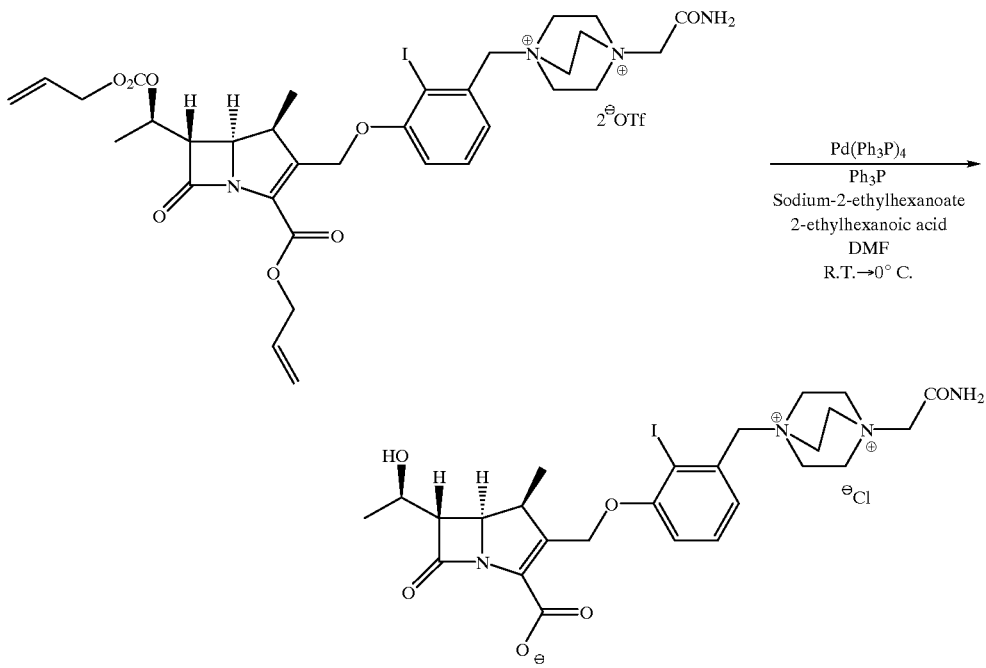

Using the analogous procedure of example 29, the bis-allyl protected dabco salt was deblocked to give the desired carbapenem.

$^1$H NMR (D$_2$O) δ: 1.41( d, J=7.4 Hz, 3H), 1.46 (d, J=6.4Hz, 3H), 3.46 (m, 1H), 3.64 (m 1H), 4.19 (bs, 6H), 4.29 (d, J=4.0 Hz, 1H), 4.43 (bs, 8H), 4.57 (m, 1H), 4.96 (s, 2H), 5.07 (d, J=14.0 Hz, 1 H), 5.80 (d, J=13.9 Hz, 1 H), 7.39–7.47 (m, 2H), 7.75 (t, J=7.6 Hz, 1H).

EXAMPLE 44

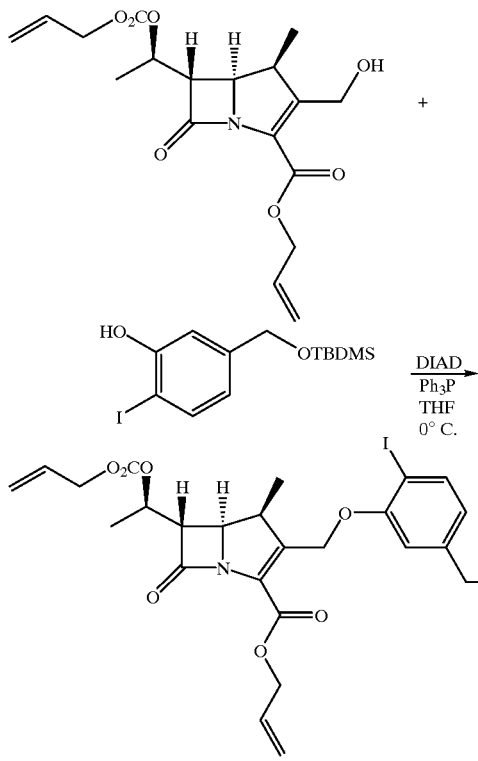

Using the analogous procedure of example 12, the bis-allyl protected carbinol was converted to the silyl ether.

$^1$H NMR (CDCl$_3$) δ: 0.094 (s, 6H), 0.929 (s, 9H), 1.27 (d, J=7.2 Hz, 3H), 1.46 (d, J=6.3 Hz, 3H), 3.43 (dd, J=3.0 Hz, 5.0 Hz, 1H), 3.60 (m, 1H), 4.20 (dd, J=3.1 Hz, 6.0 Hz, 1H), 4.63 (dd, J=1.2 Hz, 4.6 Hz, 2H), 4.64–4.867 (m, 5H), 5.11 (m, 1H), 5.265.56 (m, 5H), 5.91 (m, 2H), 6.70 (dd, J=1.8 Hz, 6.2 Hz, 1H), 6.84 (bs, 1H), 7.68 (d, J=8.0 Hz, 1H).

EXAMPLE 45

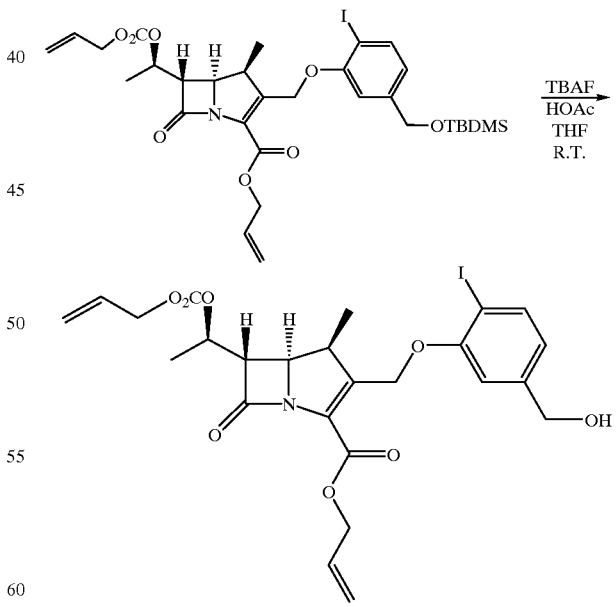

Using the analogous procedure of example 13, the silyl ether was converted to the desired carbinol.

$^1$H NMR (CDCl$_3$) δ: 1.28 (d, J=7.4 Hz, 3H), 1.46 (d, J=6.3 Hz, 3H), 3.45 (dd, J=3.0 Hz, 5.0 Hz, 1H), 3.65 (m, 1H), 4.22 (dd, J=3.0 Hz, 6.9 Hz, 1H), 4.63 (m, 4H), 4.71–4.87 (m, 3H), 5.11 (m, 1H), 5.26–5.56 (m, 5H), 5.87 (m, 2H), 6.73 (dd, J=1.8 Hz, 6.1 Hz, 1H), 6.87 (d, J=1.87 Hz, 1H), 7.73 (d, J=8.0 Hz, 1H).

EXAMPLE 46

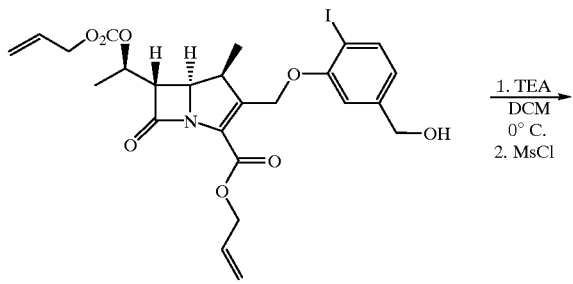

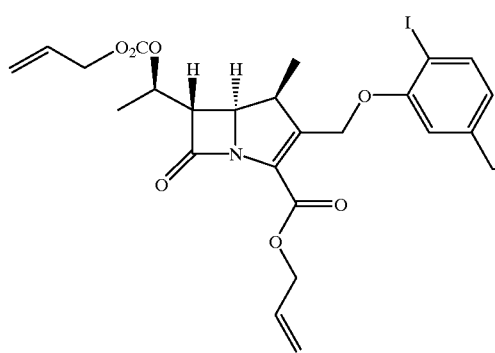

Using the analogous procedure of example 14, the benzyl alcohol was converted to the benzylic mesylate.

¹H NMR (CDCl₃) δ: 1.29 (d, J=7.2 Hz, 3H), 1.47 (d, J=6.3 Hz, 3H), 2.98 (s, 3H), 3.45 (dd, J=2.8 Hz, 4.9 Hz, 1H), 3.59 (m, 1H), 4.20 (dd, J=3.2 Hz, 6.9 Hz, 1H), 4.62 (m, 2H), 4.71–4.78 (m, 3H), 5.11 (m, 1H), 5.26–5.60 (m, 5H), 5.89–6.03 (m, 2H), 6.78 (dd, J=1.4 Hz, 6.7 Hz, 1H), 6.87 (d, J=1.6 Hz, 1H), 7.79 (d, J=7.8 Hz, 1H).

EXAMPLE 47

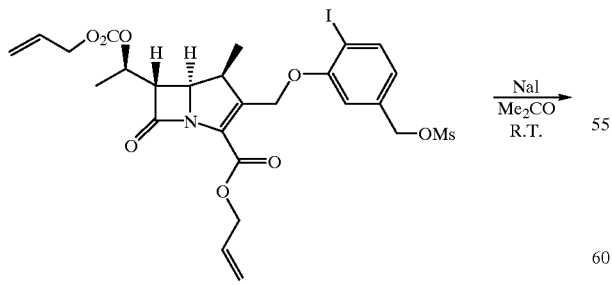

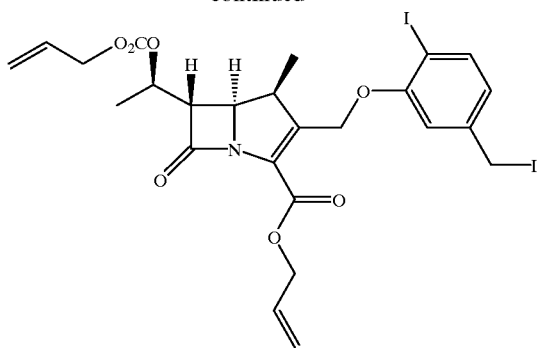

Using the analogous procedure of example 15, the benzylic mesylate was converted to the benzyl iodide.

¹H NMR (CDCl₃) δ: 1.27 (d, J=7.3 Hz, 3H), 1.46 (d, J=6.3 Hz, 3H), 3.45 (dd, J=3.0 Hz, 5.0 Hz, 1H), 3.59 (m, 1H), 4.20 (dd, J=3.0 Hz, 7.0 Hz, 1H), 4.36 (d, J=1.8 Hz, 2H), 4.61–4.65 (m, 2H), 4.71–4.89 (m, 3H), 5.18 (m, 1H), 5.26–5.57 (m, 5H), 5.87–6.04 (m, 2H), 6.75 (dd, J=2.0 Hz, 6.0 Hz, 1H), 6.83 (d, J=1.6 Hz, 1H), 7.66 (d, J=8.0 Hz, 1H).

EXAMPLE 48

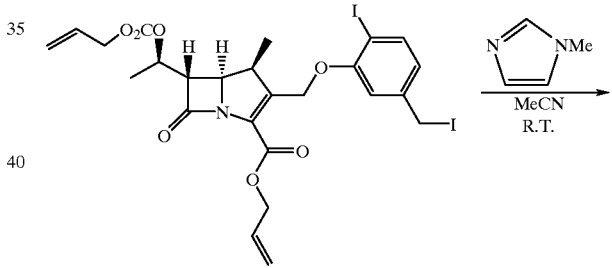

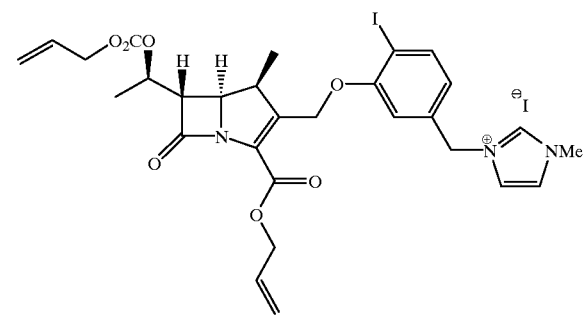

Using the analogous procedure of example 16, the benzyl iodide was converted to the imidazolium salt.

EXAMPLE 49
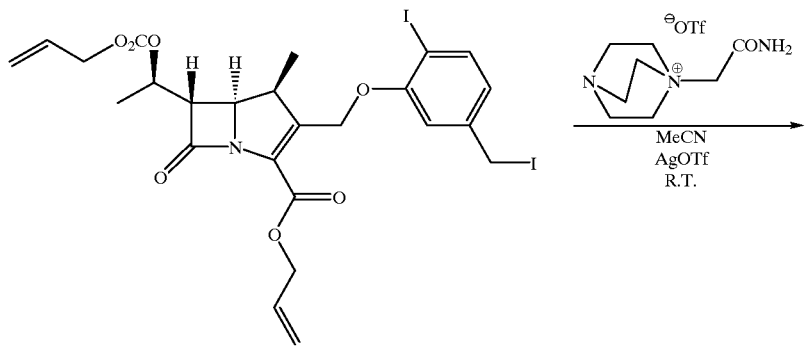
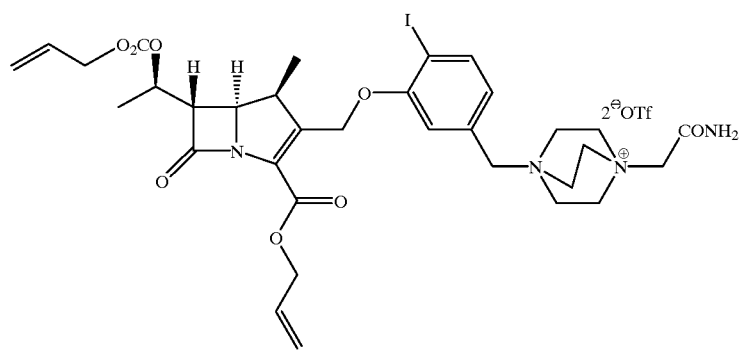
Using the analogous procedure of example 17, the benzyl iodide was converted to the triflate salt.
EXAMPLE 50
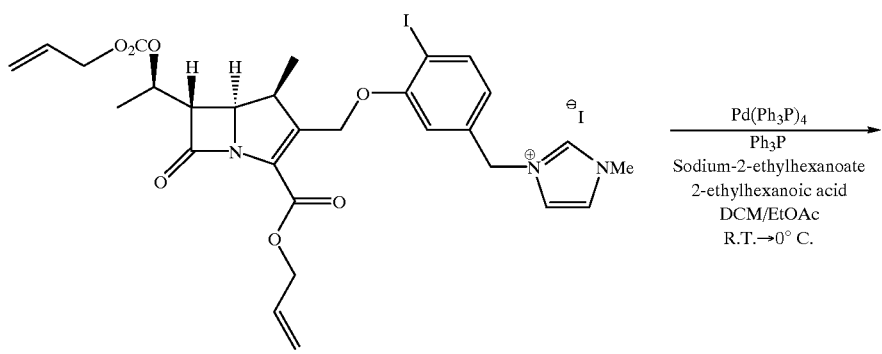
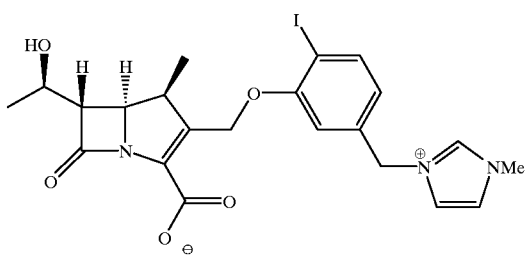

Using the analogous procedure of example 30, the bis-allyl protected imidazolim salt was deblocked to provide the desired carbapenem.

¹H NMR (D₂O) δ: 1.46 (d, J=7.1 Hz, 3H), 1.50 (d, J=6.0 Hz, 3H), 3.54 (m, 1H), 3.63 (m, 1H), 4.17 (s, 3H), 4.27 (dd, J=3.0, 7.1 Hz 1 H), 4.46 (m, 1H), 5.12 (d, J=14.2 Hz, 1H), 5.59 (d, J=3.4 Hz, 2H), 5.90 (d, J=14.2 Hz, 1H), 7.13 (d, J=9.8 Hz, 1H), 7.28 (s, 1H), 7.69 (d, J=3.0 Hz, 1H), 8.17 (d, J=8.0 Hz, 1H), 9.03 (s, 1H).

EXAMPLE 51

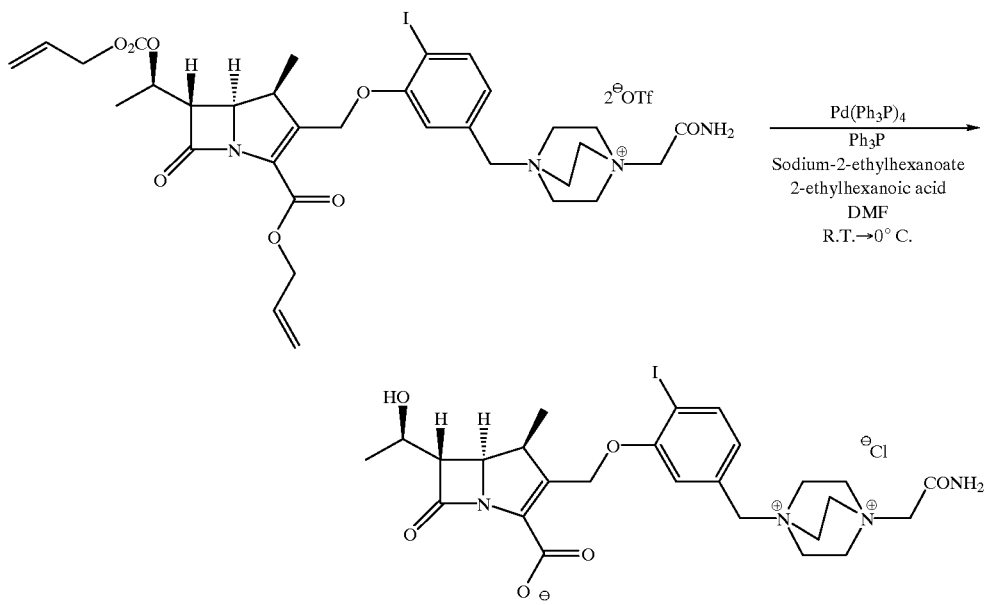

Using the analogous procedure of example 29, the bis-allyl protected dabco salt was deblocked to provide the desired carbapenem.

¹H NMR (D₂O) δ: 1.50 (m, 6H), 3.51 (m, 1H), 3.65 (m, 1H), 4.21 (m, 6H), 4.33 (dd, J=2.8 Hz, 7.3 Hz, 1H), 4.45( m, 9 H), 4.97 (s, 2H), 5.22 (d, J=14.0 Hz, 1H), 5.98 (d, J=13.8 Hz, 1H), 7.23 (d, J=8.0 Hz, 1H), 7.46 (s, 1H), 8.31 (d, J=8.0 Hz, 1H).

EXAMPLE 52

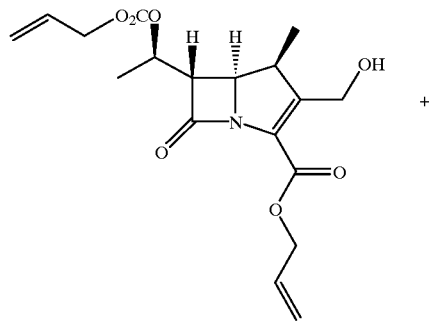

+

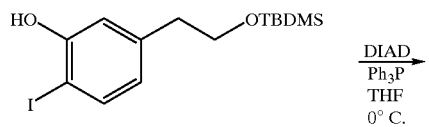

-continued

Using the analogous procedure of example 12, the bis-allyl protected carbinol was converted to the silyl ether.

¹H NMR (CDCl₃) δ: 0.088 (s, 6H), 0.869 (s, 9H), 1.27 (d, J=7.4 Hz, 3H), 1.46 (d, J=6.3 Hz, 3H), 2.73 (t, J=6.8 Hz, 2H), 3.43 (dd, J=3.0 Hz, 7.0 Hz, 1H), 3.74 (m, 1H), 3.77 (t, J=5.7 Hz, 2.0 H), 4.21 (dd, J=3.0 Hz, 7.1 Hz, 1H), 4.62 (m, 1H), 4.64 (m, 1H), 5.11 (m, 1H), 5.26–5.56 (m, 5H), 5.89 (m, 2H), 6.60 (dd, J=1.8 Hz, 6.2 Hz, 1H), 6.67 (d, J=1.8 Hz, 1H), 7.63 (d, J=8.0 Hz, 1H).

EXAMPLE 53

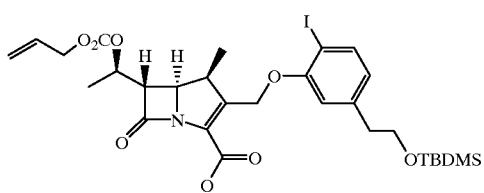

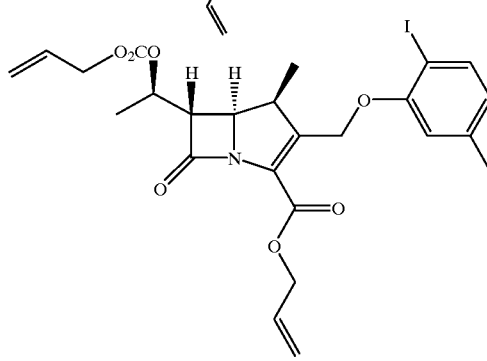

Using the analogous procedure of example 13, the silyl ether was converted to the carbinol.

¹H NMR (CDCl₃) δ: 1.29 (d, J=7.4 Hz, 3H), 1.48 (d, J=6.3 Hz, 3H), 2.83 (t, J=6.8 Hz, 2H), 3.43 (dd, J=3.0 Hz, 7.0 Hz, 1H), 3.74 (m, 1H), 3.85 (t, J=5.7 Hz, 2.0 H), 4.21 (dd, J=3.0 Hz, 7.1 Hz, 1H), 4.62 (m, 1H), 4.64 (m, 1H), 5.11 (m, 1H), 5.26–5.56 (m, 5H), 5.91 (m, 2H), 6.63 (dd, J=1.8 Hz, 6.2 Hz, 1H), 6.67 (d, J=1.8 Hz, 1H), 7.65 (d, J=8.0 Hz, 1H).

EXAMPLE 54

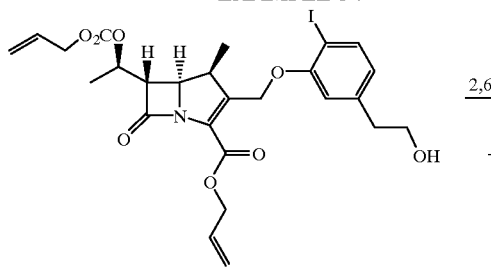

-continued

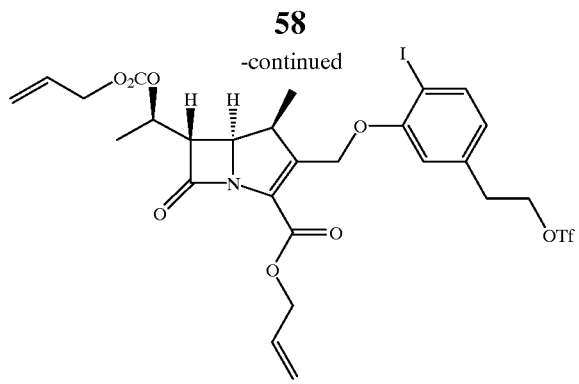

Using the analogous procedure of example 20, the carbinol was converted to the alkyl triflate.

EXAMPLE 55

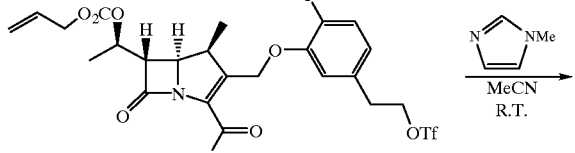

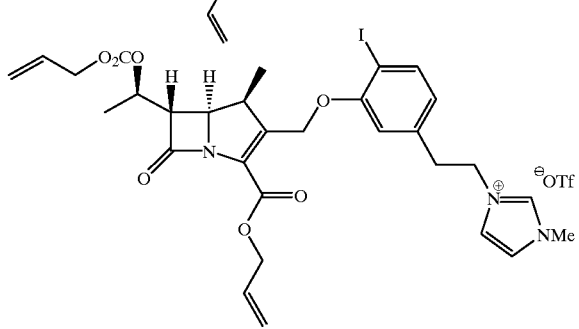

Using the analogous procedure of example 22, the alkyl triflate was converted to the imidazolium salt.

EXAMPLE 56

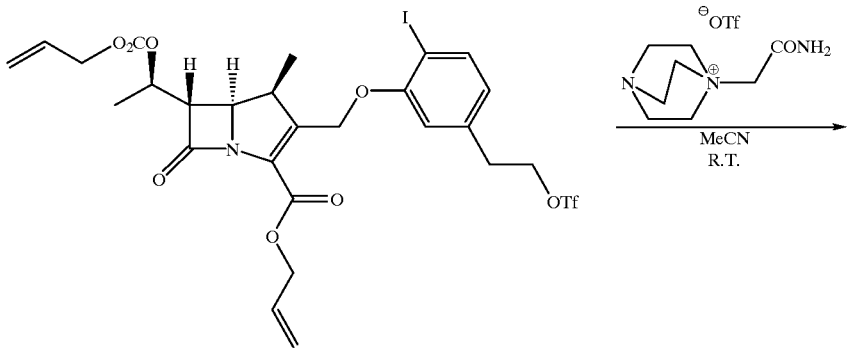

-continued
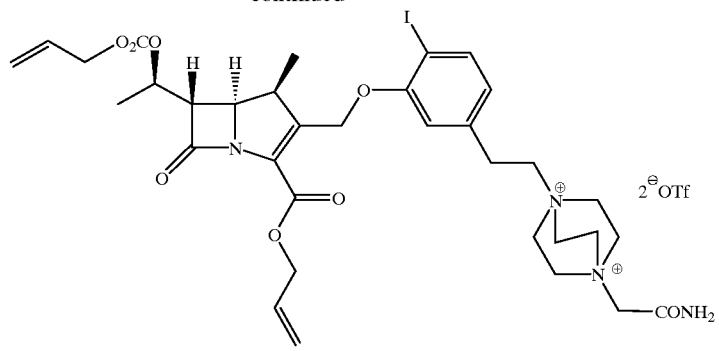
Using the analogous procedure of example 21, the alkyl triflate was converted to the triflate salt.
$^1$H NMR (D$_2$O) δ: 1.37 (d, J=7.6 Hz, 3H), 1.41 (d, J=5.8 Hz, 3H), 3.29 (t, J=6.6 Hz, 1H), 3.45 (m, 1H), 3.58 (m, 1H), 3.97 (s, 3H), 4.23 (d, J=10.0, Hz, 1 H), 4.37 (m, 1H), 4.59
EXAMPLE 57
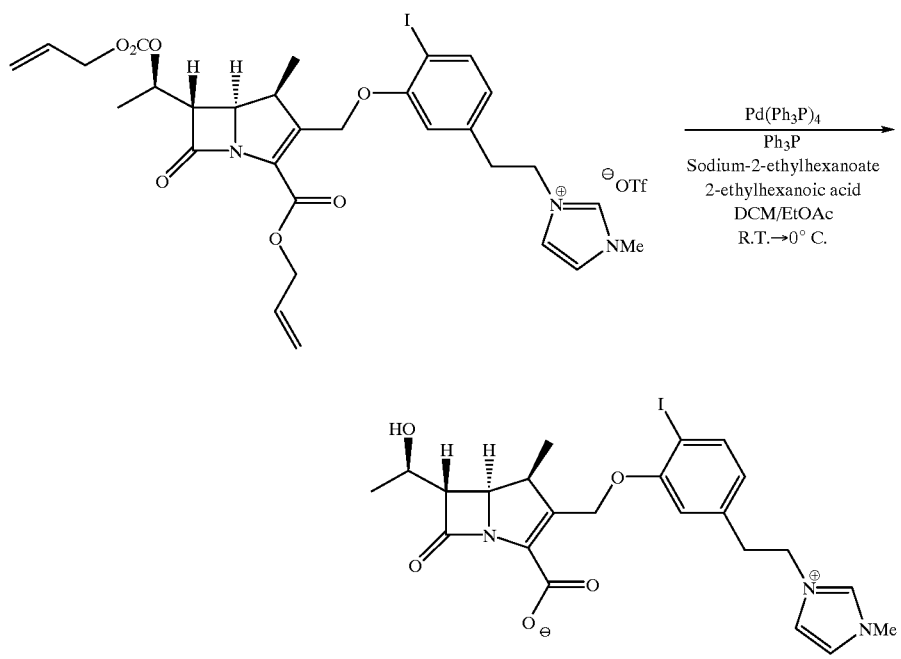
Using the analogous procedure of example 30, the bis-allyl protected imidazolium salt was deblocked to provide the desired carbapenem.
(t, J=6.1 Hz, 2H), 4.90 (d, J=14.0 Hz, 1H), 5.74 (d, J=14.9 Hz, 1H), 6.97 (s, 1H), 7.51 (s, 1H), 7.54 (s, 1H), 7.93 (d, J=6.4 Hz, 1H), 8.84 (s, 1H).

EXAMPLE 58

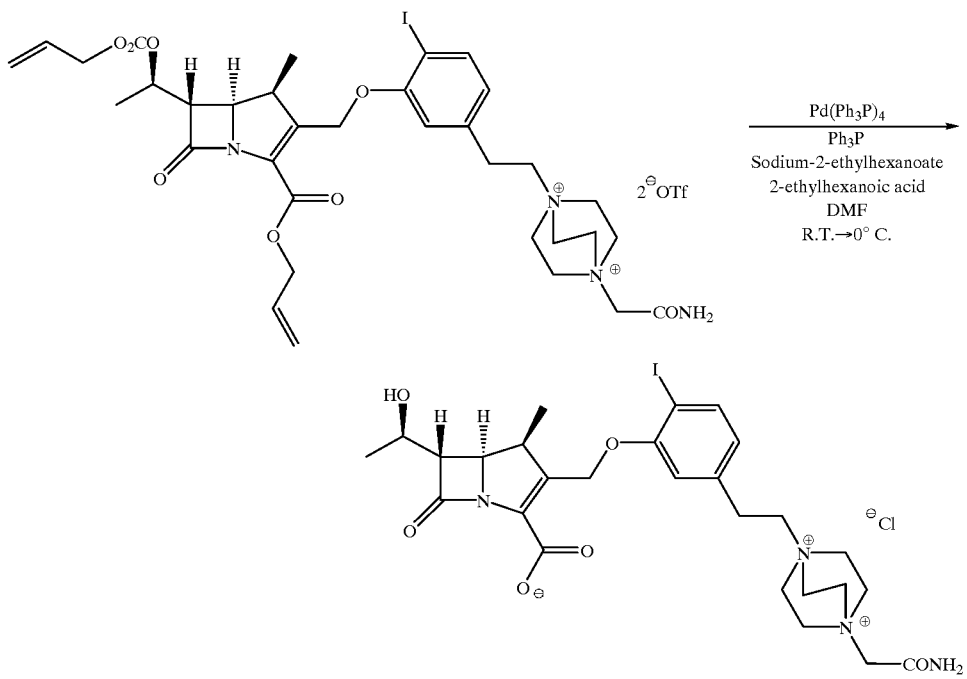

Using the analogous procedure of example 29, the bis-allyl protected dabco salt was deblocked to provide the desired carbapenem.

$^1$H NMR (D$_2$O) δ: 1.49 (t, J=7.3 Hz, 6H), 3.37 (m, 3H), 3.66 (m, 1H), 4.00–4.08 (m, 1H), 4.23 4.38 (m, 6H), 4.4 (m, 1H), 4.45( m, 9 H), 4.53 (m, 9H), 5.14 (d, J=14.0 Hz, 1H), 5.98 (d, J=14.2 Hz, 1H), 7.05 (d, J=8.0 Hz, 1H), 7.31 (s, 1H), 8.10 (d, J=7.8 Hz, 1H).

What is claimed is:

1. A compound represented by formula I:

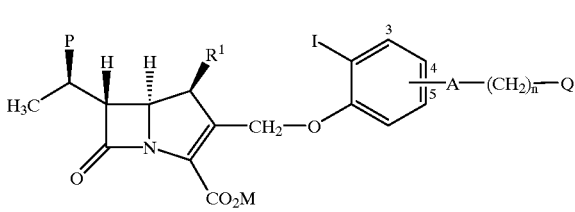

as well as salts and hydrates thereof, wherein:

the compound contains no more than two positive charges balanced by two negative charges to provide overall charge neutrality to the compound;

R$^1$ represents H or methyl;

CO$_2$M represents a carboxylic acid, a carboxylate anion, balanced by a counterion, or a pharmaceutically acceptable ester group;

P represents hydrogen, hydroxyl or F;

A represents O, S or —CH$_2$— attached at position 3, 4 or 5;

n represents an integer from 0–3;

Q is selected from the group consisting of:

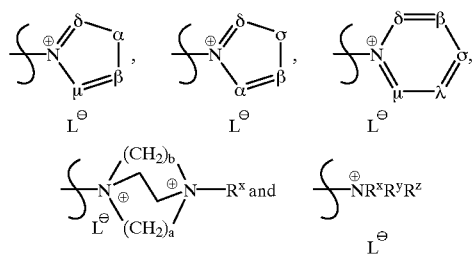

wherein:

no more than 2 quaternary nitrogens are present on a and b are 1, 2 or 3;

L$^-$ is a pharmaceutically acceptable counterion present or absent as necessary to maintain the appropriate charge balance;

a represents O, S or NR$^s$;

β, δ, γ, μ and σ represent CR$^t$, N or N+R$^s$, provided that no more than one of β, δ, γ, μ and σ is N+R$^s$, balanced by L$^-$;

each R$^s$ independently represents hydrogen; phenyl or —C$_{1-6}$ straight- or branched- chain alkyl, unsubstituted or substituted with one to four R$^i$ groups;

each R$^t$ independently represents hydrogen; halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; NRUSO$_2$R$^v$; —COR$^u$; —NR$^u$COR$^v$; —OCOR$^u$; —OCONR$^u$R$^v$; —NR$^u$C$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

each R$^i$ independently represents halo; —CN; —NO$_2$; phenyl; —NHSO$_2$R$^h$; —OR$^h$, —SR$^h$; —N(R$^h$)$_2$; —N+, —C(O)N($R^h$)$_2$; —SO$_2$N($R^h$)$_2$; heteroaryl; heteroarylium, balanced by a counterion; —CO$_2$$R^h$; —C(O)$R^h$; —OCO$R^h$; —NHCO$R^h$; guanidinyl; carbamirnidoyl or ureido;

each $R^h$ independently represents hydrogen, a —C$_{1-6}$ straight or branched-chain alkyl group, a —C$_3$–C$_5$ cycloalkyl group or phenyl, or when two $R^h$ groups are present;

$R^u$ and $R^v$ represent hydrogen or —C$_{1-6}$ straight- or branched-chain alkyl, unsubstituted or substituted with one to four $R^i$ groups;

each $R^w$ independently represents hydrogen; —C$_{1-6}$ straight- or branched-chain alkyl, unsubstituted or substituted with one to four $R^i$ groups; C$_{3-5}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a C$_{1-8}$ straight- or branched-chain alkyl, optionally interrupted by one or two of O, S, SO, SO$_2$, N$R^w$, or —C(O)—, said chain being unsubstituted or substituted with one to four of halo, CN, NO$_2$, O$R^w$, S$R^w$, SO$R^w$, SO$_2$$R^w$, N$R^h$$R^w$, —C(O)—$R^w$, C(O)N$R^h$$R^w$, SO$_2$N$R^h$$R^w$, CO$_2$$R^w$, OC(O)$R^w$, OC(O)N$R^h$$R^w$, N$R^h$C(O)$R^w$, N$R^h$C(O)N$R^h$$R^w$, or a phenyl or heteroaryl group which is in turn optionally substituted with from one to four $R^i$ groups or with one to two C$_{1-3}$ straight- or branched- chain alkyl groups, said alkyl groups being unsubstituted or substituted with one to four $R^i$ groups; and $R^y$ and $R^z$ represent hydrogen; phenyl; —C$_{1-6}$ straight or branched chain alkyl, unsubstituted or substituted with one to four $R^i$ groups, and optionally interrupted by O, S, N$R^w$, or —CO).

2. A compound in accordance with claim 1 wherein $R^1$ represents methyl.

3. A compound in accordance with claim 1 wherein CO$_2$M represents a carboxylic acid or a carboxylate anion.

4. A compound in accordance with claim 1 wherein P represents hydroxyl.

5. A compound in accordance with claim 1 wherein A represents —CH$_2$—.

6. A compound in accordance with claim 1 wherein n represents 0 or 1.

7. A compound in accordance with claim 1 wherein Q represents

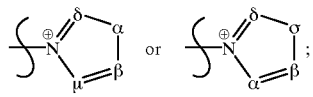

wherein:

α represents O, S or N$R^s$;

β, δ, μ and σ represent C$R^t$, N or N+$R^s$, provided that no more than one of β, δ, μ and σ is N+$R^s$, balanced by L$^-$ which is a pharmaceutically acceptable counterion, and $R^s$ is as originally defined.

8. A compound in accordance with claim 1 wherein Q is selected from the group consisting of:

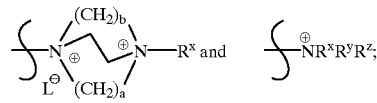

a and b are 2;

L— is a pharmaceutically acceptable counterion;

and $R^x$, $R^y$ and $R^z$ are as originally defined.

9. A compound in accordance with claim 8 wherein Q is

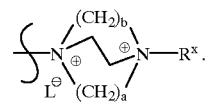

10. A compound in accordance with claim 1 wherein Q is

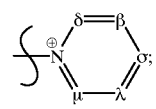

wherein:

α represents O, S or N$R^s$;

β, δ, γ, μ and σ represent C$R^t$, N or N+$R^s$, provided that no more than one of β, δ, γ, μ and σ is N+$R^s$, balanced by L$^-$, which is a pharmaceutically acceptable counterion, and all other variables are as originally defined.

11. A compound in accordance with claim 1 falling within the following table:

TABLE 1

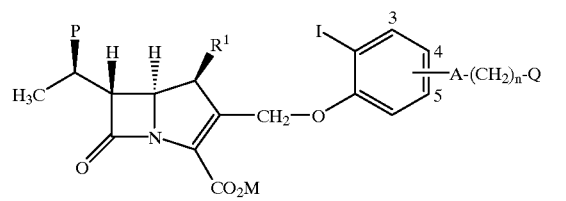

| Cpd No. | A-(CH$_2$)$_n$-Q |
|---|---|
| 1 | 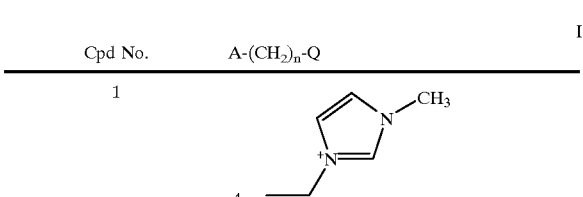 4- |
| 2 | 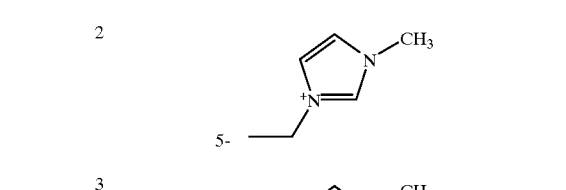 5- |
| 3 | 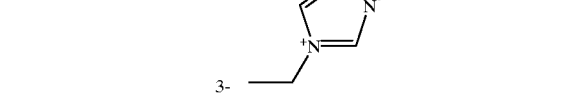 3- |

TABLE 1-continued
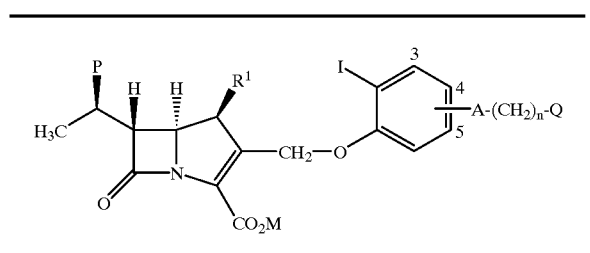
| Cpd No. | A-(CH$_2$)$_n$-Q |
|---|---|
| 4 | 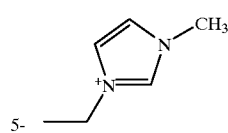 |
| 5 | 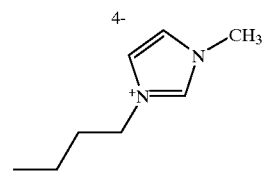 |
| 6 | 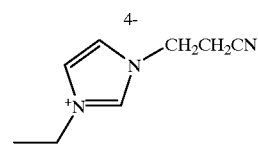 |
| 7 | 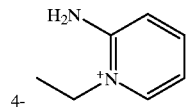 |
TABLE 1-continued
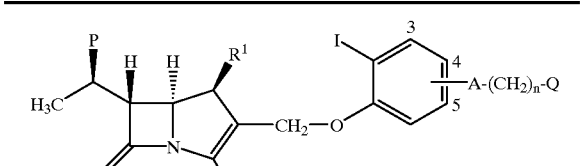
| Cpd No. | A-(CH$_2$)$_n$-Q |
|---|---|
| 8 | 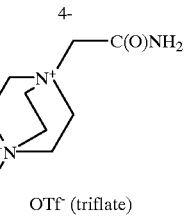 |
| 9 | 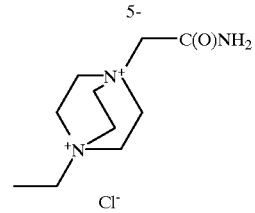 |
| 13 | 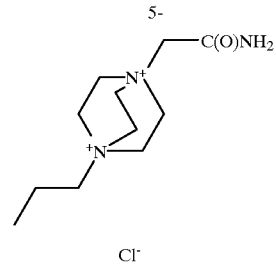 |
12. A compound in accordance with claim 1 falling within table 2:
TABLE 2
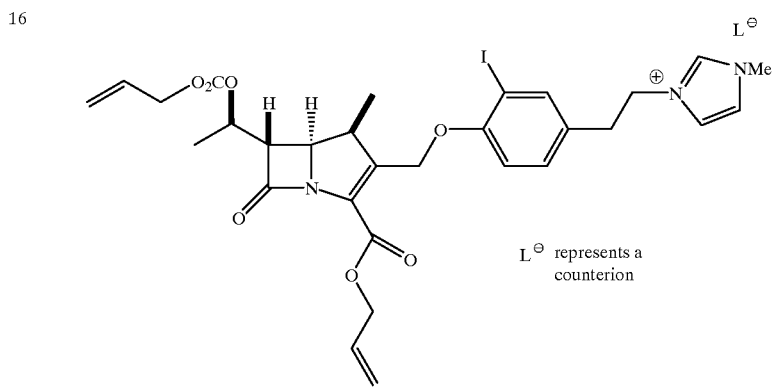
$L^{\ominus}$ represents a counterion TABLE 2-continued
22
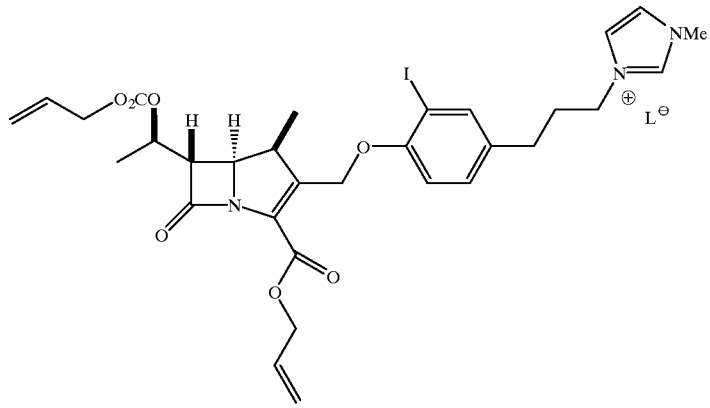
27
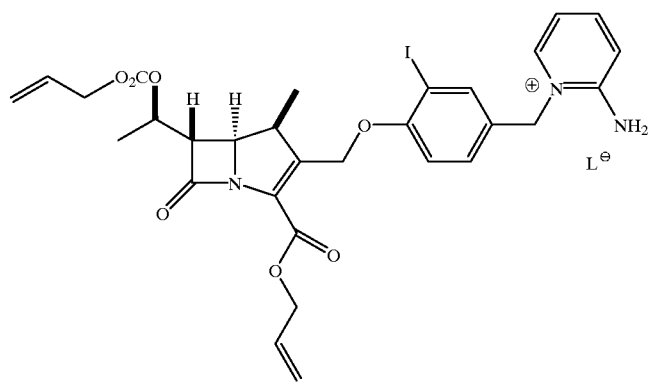
28
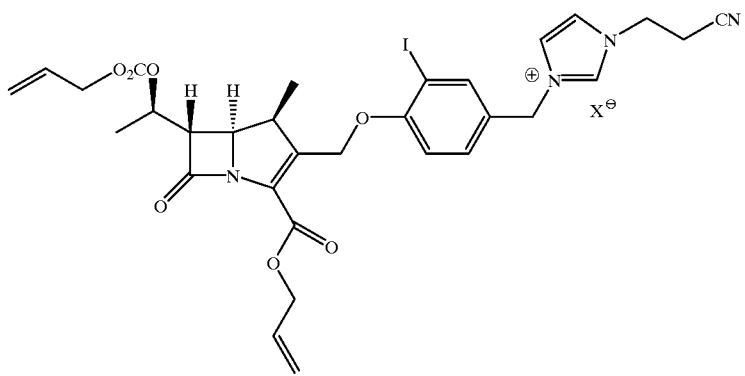
29
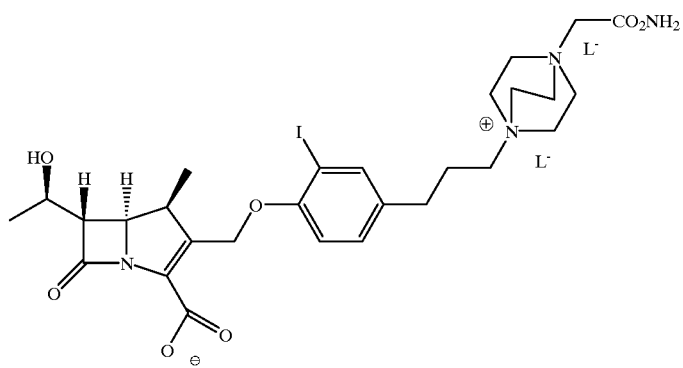

TABLE 2-continued
30 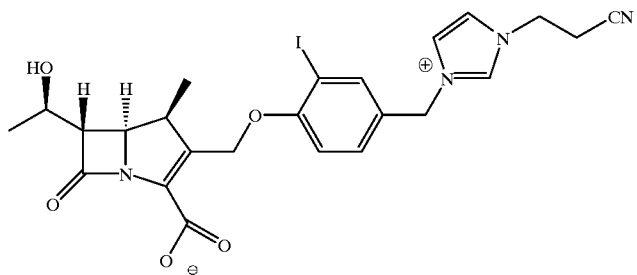
31 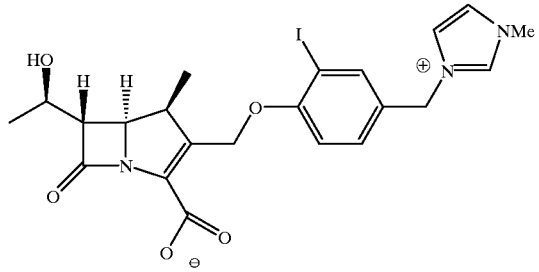
32 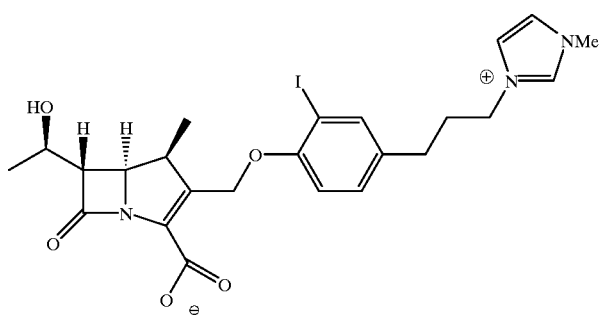
33 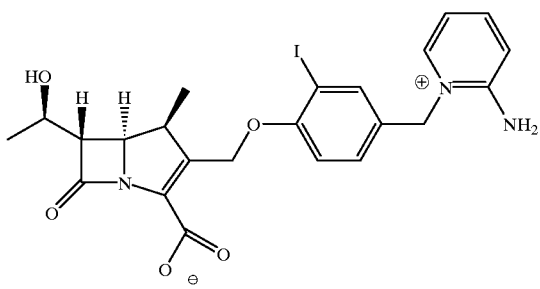
34 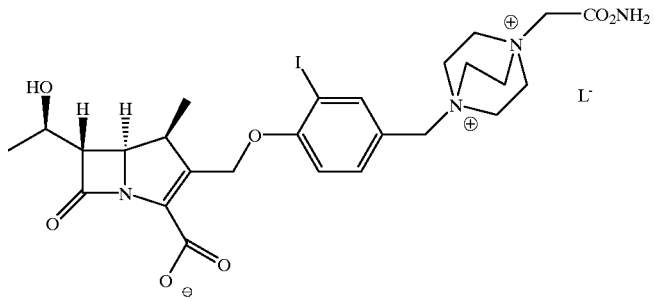

TABLE 2-continued
35
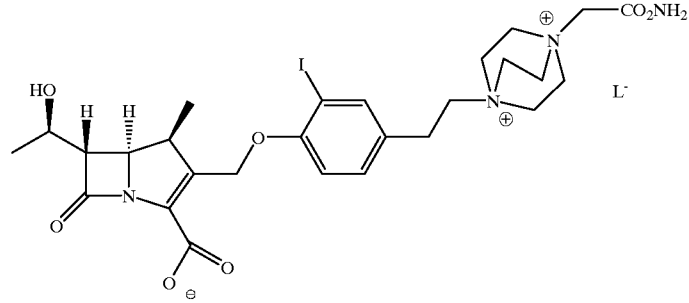
40
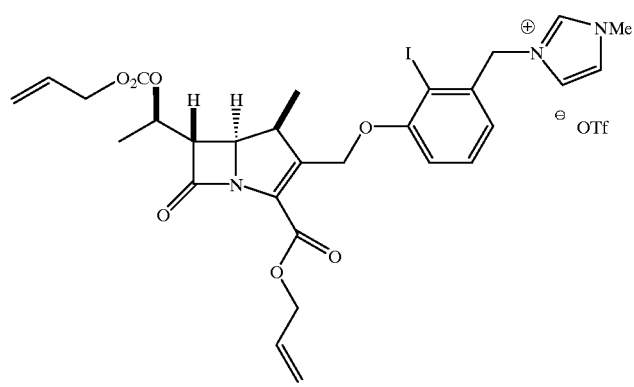
41
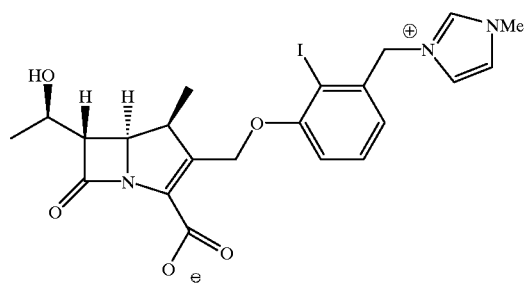
43
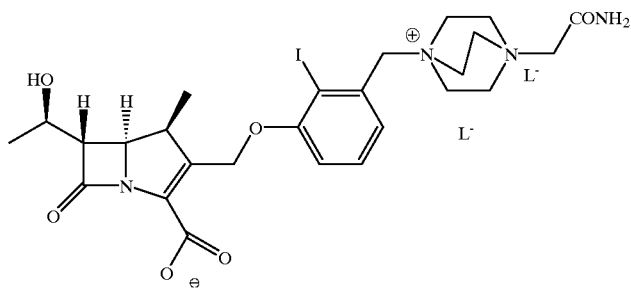

TABLE 2-continued
48
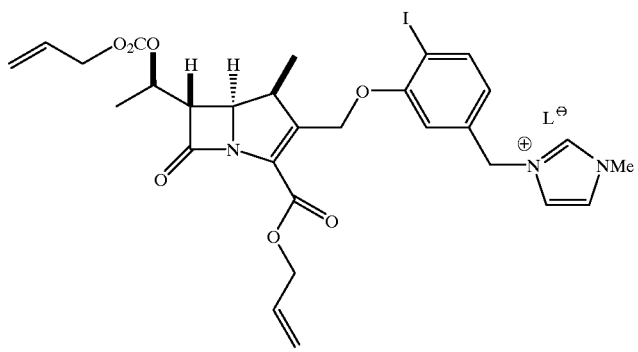
50
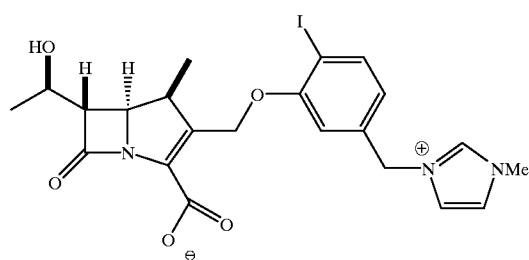
51
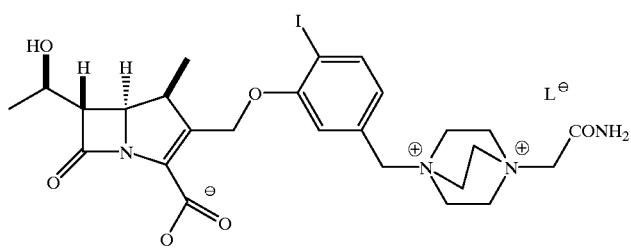
55
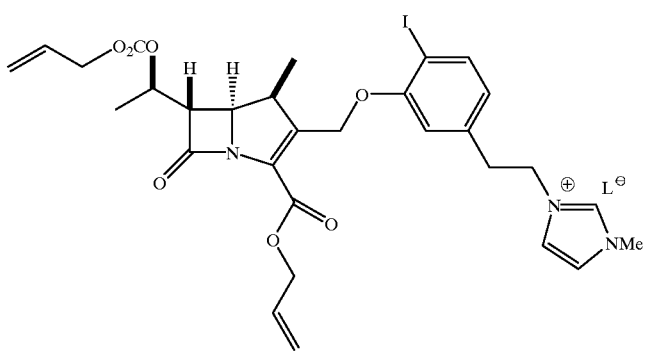
57
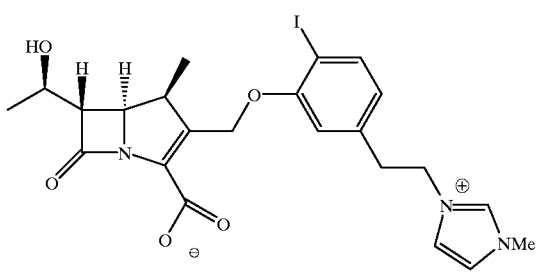

TABLE 2-continued

58

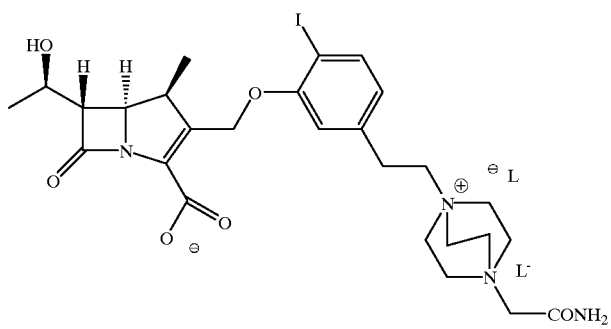

wherein X⁻ represents a counterion.

13. A pharmaceutical composition which is comprised of a compound in accordance with claim 1, or a pharmaceutically acceptable salt or hydrate thereof, in combination with a pharmaceutically acceptable carrier.

14. A method of treating or preventing a bacterial infection in a mammalian patient in need of such therapy, comprising administering to said patient an anti-infective amount of a compound as defined in claim 1.

15. A pharmaceutical composition in accordance with claim 13 further comprised of a compound which inhibits dehydropeptidase.

* * * * *